US012681008B2

(12) United States Patent
Park et al.

(10) Patent No.: US 12,681,008 B2
(45) Date of Patent: Jul. 14, 2026

(54) FLUORESCENT COMPOUND FOR IMMUNOHISCHEMISTRY AND DIAGNOSIS COMPOSITION FOR DETECTING BIOLOGICAL MATERIAL COMPRISING THE SAME

(71) Applicant: BIOACTS CORPORATION, Incheon (KR)

(72) Inventors: Jin Woo Park, Incheon (KR); Kiwon Kim, Incheon (KR); Su Jung Jang, Incheon (KR); Mina Kim, Incheon (KR)

( * ) Notice: Subject to any disclaimer, the term of this patent is extended or adjusted under 35 U.S.C. 154(b) by 783 days.

(21) Appl. No.: 18/073,644

(22) Filed: Dec. 2, 2022

(65) Prior Publication Data

US 2024/0201177 A1 Jun. 20, 2024

(30) Foreign Application Priority Data

Nov. 24, 2022 (KR) ........................ 10-2022-0159567

(51) Int. Cl.
*G01N 33/533* (2006.01)
*C07D 403/14* (2006.01)

(52) U.S. Cl.
CPC ......... *G01N 33/533* (2013.01); *C07D 403/14* (2013.01)

(58) Field of Classification Search
CPC .... G01N 33/533; C07D 403/14; C09K 11/06; C09B 23/06; C09B 23/083; C09B 23/107
See application file for complete search history.

(56) References Cited

FOREIGN PATENT DOCUMENTS

KR 10-1944912 B1 1/2019

OTHER PUBLICATIONS

Gidi et al., J. Am. Chem. Soc. 2020, 142 pp. 12681-12689.*

* cited by examiner

*Primary Examiner* — Alicia L Otton

(57) ABSTRACT

Provided is a fluorescent compound for labeling a biomaterial having the following Chemical Formula 1:

[Chemical Formula 1]

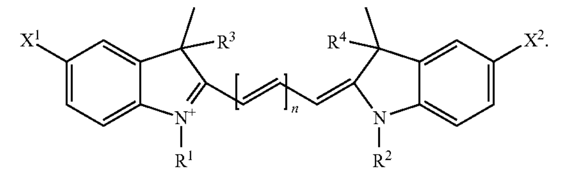

In Chemical Formula 1 above, n is an integer of 1 to 6; $X^1$ and $X^2$ are the same as or different from each other, and each independently selected from H, $SO_3^-$ and $SO_3H$; $R^1$ and $R^2$ are the same as each other or each independently selected from $C_{1-7}$ alkyl, substituted or unsubstituted $C_{8-20}$ alkyl, $—(CH_2)_{m1}SO_3^-$, $—(CH_2)_{m2}SO_3H$, and

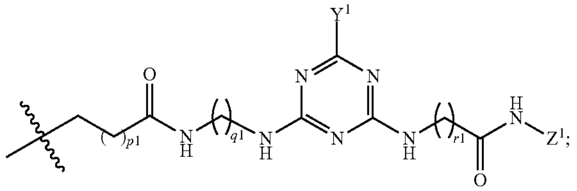

m1 is an integer of 1 to 7, m2 is an integer of 1 to 7; p1 is an integer of 1 to 10; r1 is an integer of 1 to 10; and $Y^1$ is selected from H, —OH, halogen and

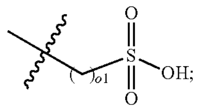

o1 is an integer of 1 to 10.

5 Claims, 1 Drawing Sheet

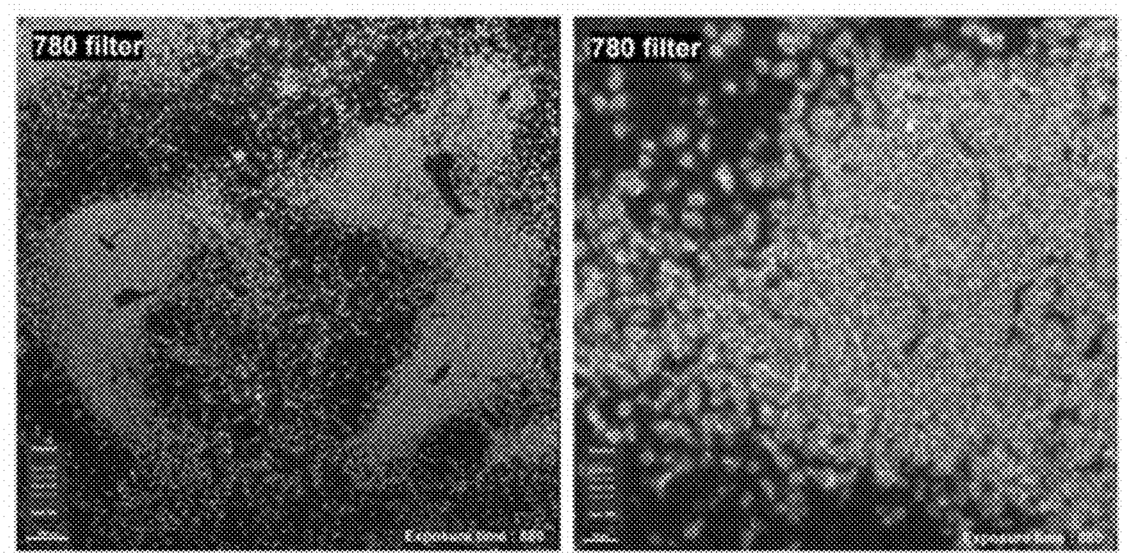
(left) 780 filter, 100X image, (right) 780 filter, 400X image

FLUORESCENT COMPOUND FOR IMMUNOHISCHEMISTRY AND DIAGNOSIS COMPOSITION FOR DETECTING BIOLOGICAL MATERIAL COMPRISING THE SAME

CROSS-REFERENCE TO RELATED APPLICATIONS

This application claims priority from and the benefit of Korean Patent Application No. 10-2022-0159567, filed on Nov. 24, 2022, which is hereby incorporated by reference for all purposes as if fully set forth herein.

BACKGROUND

Field

The present disclosure relates to a fluorescent compound for immunohistochemistry, which is a compound that is useful for a fluorescent diagnosis composition capable of prediction, diagnosis, treatment and prognosis of diseases.

The fluorescent compound of chemical formula 1 provided in exemplary embodiments of the present invention is for immunohistochemistry for detecting and diagnosing disease. By using the chemical, it is possible to analyze the genotype and space simultaneously and to more delicately and effectively analyze the biomaterials at the level of low molecular protein, antibody, DNA, RNA etc. because of simultaneous staining of multi-markers in one slide.

Description of the Related Art

Since a biomaterial itself has weak fluorescence or no fluorescence in visible and near-infrared regions, in the biotech field, in order to observe biological phenomena at cellular and subcellular levels in vivo or in vitro or to make images and obtain optical images of a diseased area by being projected into a living body, imaging data have been obtained through a variety of methods using a fluorescent dye or a specific biomaterial pre-labeled with the fluorescent dye in the biomaterial with optical equipment.

Various optical analysis devices used in the biotech field select a fluorescent dye with an excitation wavelength and an emission wavelength suitable for observing fluorescence according to embedded light sources and filters as a basic material or reagent.

In general, most of fluorescent dyes used for labeling biomolecules such as proteins or peptides include structures, such as anthranilate, 1-alkylthic isoindoles, pyrrolinones, bimanes, benzoxazole, benzimidazole, benzofurazan, naphthalenes, coumarins, cyanine, stilbenes, carbazoles, phenanthridine, anthracenes, bodipy, fluoresceins, eosins, rhodamines, pyrenes, chrysenes and acridines.

When selecting a fluorescent dye structure usable in the biotech field from the plurality of fluorescent chromophores illustrated above, generally, it is important to emit strong fluorescence when most of the biomolecules exist in the medium, which is typically an aqueous solution and an aqueous buffer, and to have excitation and fluorescence wavelengths suitable for fluorescence equipment.

Dyes that may be mainly applied in the biotech field need to preferably have less photobleaching and quenching in aqueous or hydrophilic conditions, to have a large molecular extinction coefficient so as to absorb a large amount of light, to be in the visible or near-infrared region of 500 nm or more far from the fluorescence range of the biomolecule itself, and to be stable under various pH conditions. However, structures of dyes usable for labeling biomolecules capable of satisfying the limitations are limited.

Fluorescent chromogens that meet these requirements include cyanine, rhodamine, flocseine, bodipy, coumarin, acridine, and pyren derivatives, and introduce functional groups so as to bind to a dye alone or a specific substituent in a biomolecular structure. Among them, xanthane-based flocseine and rhodamine, and polymethine-based cyanine derivative dye compounds have mainly been commercialized.

In particular, the dye compound having the cyanine chromophore has an advantage that it is easy to synthesize compounds having various absorption/excitation wavelengths. In addition, generally, since the dye compound having the cyanine chromophore is excellent in optical and pH stability, has narrow absorption and emission wavelength ranges, and has a fluorescent area of 500 to 800 nm, the dye compound is not overlapped with the self-fluorescent region of the biomolecule to be easily analyzed and has a slight difference according to a solvent and solubility characteristics, but has many advantages such as representing high molar adsorption coefficient, and thus is frequently used for biological applications.

In addition, the dye compound having the cyanine chromophore may also be usefully employed for optical filters for image display devices or resin compositions for laser fusion. The compound having a large intensity of absorption in specific light has been widely used as an optical element of an optical filter for an image display device such as a liquid crystal display device, a plasma display panel, an electroluminescence display, a cathode tube display panel, and a fluorescent display tube or an optical recording medium of DVD+R and the like. The optical filter has required a function of selectively absorbing light having unnecessary wavelengths, and simultaneously has required light absorption of wavelengths of 480 to 500 nm and 540 to 800 nm to prevent reflections or glare of external light such as fluorescent light, and has required a function of selectively absorbing wavelengths of infrared light in order to increase the image quality.

Therefore, in order to usefully apply the dyes industrially, it has been continuously required to develop novel dyes that have excellent optical and pH stability, have a narrow absorption/emission wavelength range in a specific wavelength range, and exhibit a high molar absorption coefficient.

Meanwhile, surgical pathology is the field of analyzing the biopsy tissue and surgical extract from a patient, and cell pathology is the field of diagnosing cells from decidual cells or fine needle aspiration cells. A normal method for tissue diagnosis is hematoxylin-eosin staining. However, it is difficult to find out the cause and prognosis of disease or positivity of malignity of tumor.

To solve this drawback, histochemistry, immunohistochemistry and in situ load method are normally used. Polymerase chain reaction and gene sequencing analysis are sometimes used as needed.

Immunochemical staining is the method of detecting a part of a cell where an antigen exists by applying the property of an antibody attaching a specific antigen.

The antigen-antibody conjugate can be observed using the color of a marker attached the conjugate because it is too difficult to observe the antigen-antibody conjugate itself.

SUMMARY

An object of the present invention is to provide a fluorescent compound for immunohistochemistry which can analyze the genotype and space simultaneously and to more delicately and effectively analyze the biomaterials at the level of protein as the final product of DNA, RNA, antibody which are the biological targets because of simultaneous staining of multi-markers in one slide and the process for analysis by using the fluorescent compound in the present invention is the same as that of pathological analysis in the prior arts.

In order to solve the above-described problems, the inventors of the present application have developed a fluorescent compound represented by the following Chemical Formula 1 in one exemplary of the present invention.

[Chemical Formula 1]

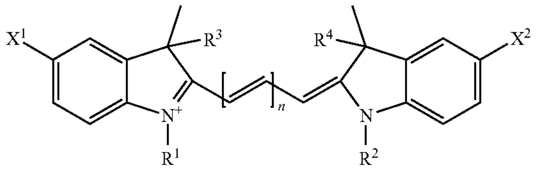

In Chemical Formula 1 above, n is an integer of 1 to 6, $X^1$ and $X^2$ are the same as or different from each other, and each independently selected from H, $—SO_3^-$ and $—SO_3H$, $R^1$ and $R^2$ are the same as each other or each independently selected from C1-7 alkyl, substituted or unsubstituted $C_{8-20}$ alkyl, $—(CH_2)_{m1}SO_3^-$, $—(CH_2)_{m2}SO_3H$, and

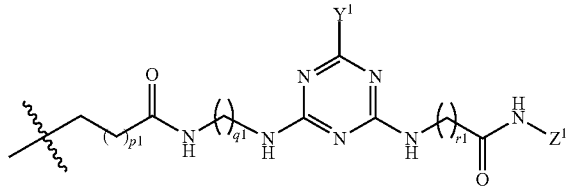

m1 is an integer of 1 to 7, m2 is an integer of 1 to 7, p1 is an integer of 1 to 10, q1 is an integer of 0 to 10, r1 is an integer of 1 to 10, and $Y^1$ is selected from H, —OH, halogen and

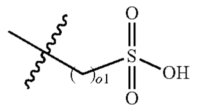

o1 is an integer of 1 to 10, $Z^1$ is selected from H, $C_{1-7}$ alkyl, substituted or unsubstituted $C_{8-20}$ alkyl and

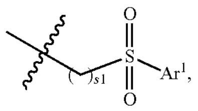

s1 is an integer of 1 to 10, and $Ar^1$ is selected from H, $C_{1-7}$ alkyl, substituted or unsubstituted $C_{8-20}$ alkyl, $C_{1-7}$ aminoalkyl and

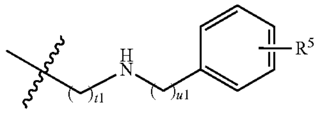

t1 is an integer of 1 to 10, u1 is an integer of 1 to 10, and $R_5$ is selected from H, OH, $C_{1-7}$ alkyl, substituted or unsubstituted $C_{8-20}$ alkyl, and $R^3$ and $R^4$ are the same as or different from each other and each independently selected from substituted or unsubstituted $C_{1-7}$ alkyl, substituted, unsubstituted $C_{8-20}$ alkyl and

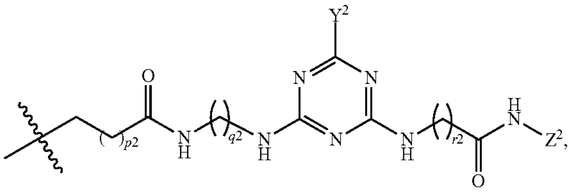

p2 is an integer of 1 to 10, q2 is an integer of 1 to 10, r2 is an integer of 1 to 10, and $Y^2$ is selected from H, —OH, halogen and

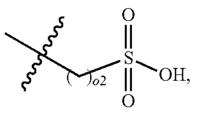

o2 is an integer of 1 to 10, $Z^2$ is selected from H, substituted or unsubstituted $C_{1-7}$ alkyl, substituted or unsubstituted $C_{8-20}$ alkyl and

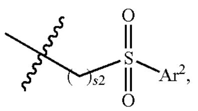

s2 is an integer of 1 to 10, and $Ar^2$ is selected from H, substituted or unsubstituted $C_{1-7}$ alkyl, substituted or unsubstituted $C_{8-20}$ alkyl, $C_{1-7}$ aminoalkyl and

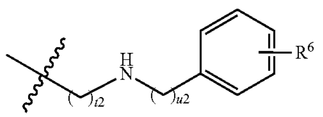

and t2 is an integer of 1 to 10, u2 is an integer of 1 to 10, $R^6$ is selected from H, —OH, substituted or unsubstituted $C_{1-7}$ alkyl and substituted or unsubstituted $C_{8-20}$ alkyl.

Preferably in the chemical formula 1, n is an integer of 1 to 3, $X^1$ and $X^2$ are the same as or different from each other, and each independently selected from —$SO_3^-$ and —$SO_3H$, $R^1$ and $R^2$ are the same as each other or each independently selected from $C_{1-4}$ straight chain alkyl, —$(CH_2)_{m1}SO_3^-$, —$(CH_2)_{m2}SO_3H$, and

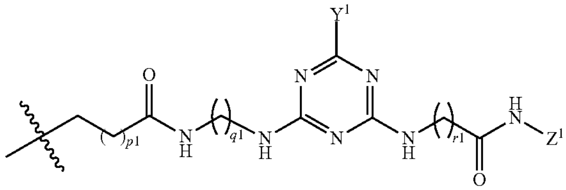

m1 is an integer of 1 to 5, m2 is an integer of 1 to 5, p1 is an integer of 1 to 5, q1 is an integer of 1 to 6, r1 is an integer of 1 to 6, and $Y^1$ is selected from —OH, —$Cl^-$ and

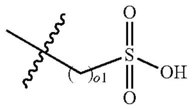

o1 is an integer of 1 to 4, $Z^1$ is selected from H, $C_{1-4}$ straight chain alkyl and

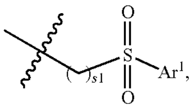

s1 is an integer of 1 to 4, and $Ar^1$ is selected from $C_{1-4}$ straight chain alkyl, $C_{1-4}$ aminoalkyl and

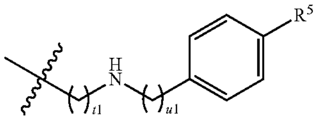

t1 is an integer of 1 to 4, u1 is an integer of 1 to 4, $R^5$ is selected from H, OH, $C_{1-4}$ straight chain alkyl.

More preferably, $R^3$ and $R^4$ are the same as or different from each other and each independently selected from substituted or unsubstituted $C_{1-7}$ alkyl, substituted, unsubstituted $C_{8-20}$ alkyl and

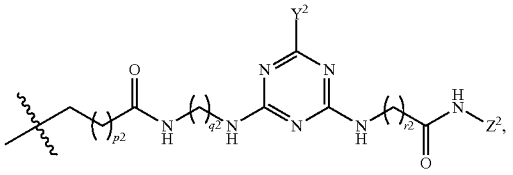

p2 is an integer of 1 to 10, q2 is an integer of 1 to 10, r2 is an integer of 1 to 10, and $Y^2$ is selected from H, —OH, halogen and

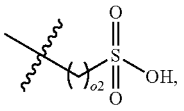

o2 is an integer of 1 to 10, $Z^2$ is selected from H, substituted or unsubstituted $C_{1-7}$ alkyl, substituted or unsubstituted $C_{8-20}$ alkyl and

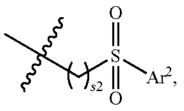

s2 is an integer of 1 to 10, and $Ar^2$ is selected from H, substituted or unsubstituted $C_{1-7}$ alkyl, substituted or unsubstituted $C_{8-20}$ alkyl, $C_{1-7}$ aminoalkyl and

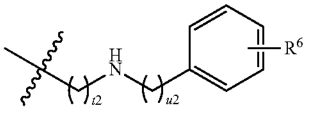

and t2 is an integer of 1 to 10, u2 is an integer of 1 to 10, $R^6$ is selected from H, —OH, substituted or unsubstituted $C_{1-7}$ alkyl and substituted or unsubstituted $C_{8-20}$ alkyl.

More and more preferably in the chemical formula 1, $R^3$ and $R^4$ are the same as or different from each other and each independently selected from $C_{1-4}$ straight chain alkyl and

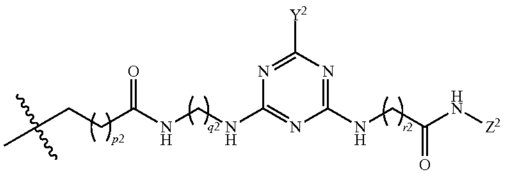

and p2 is an integer of 1 to 5, q2 is an integer of 1 to 5, r2 is an integer of 1 to 6, and $Y^2$ is selected from —OH, —$Cl^-$ and

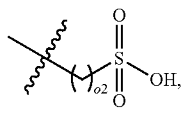

o2 is an integer of 1 to 4, $Z^2$ is selected from H, $C_{1-4}$ straight chain alkyl and

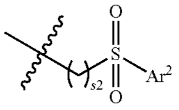

and, s2 is an integer of 1 to 4, and $Ar^2$ is selected from $C_{1-4}$ straight chain alkyl, $C_{1-4}$ amino-alkyl and

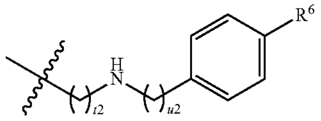

and t2 is an integer of 1 to 4, u2 is an integer of 1 to 6, $R^6$ is selected from H, OH, $C_{1-4}$ straight chain alkyl.

The most preferably, the chemical represented by the formula 1 is the chemical selected from chemicals 1-12 below.

1

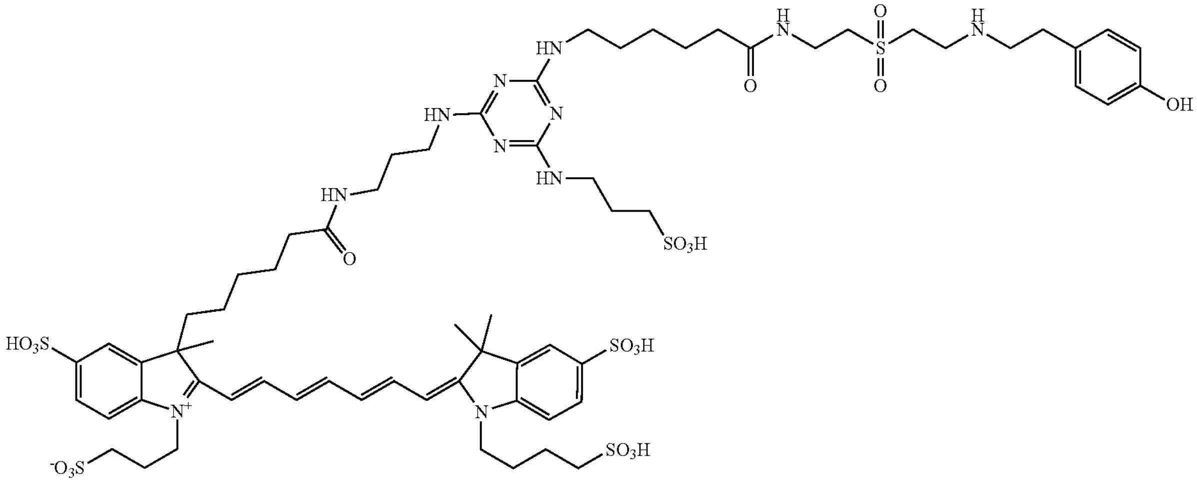

2

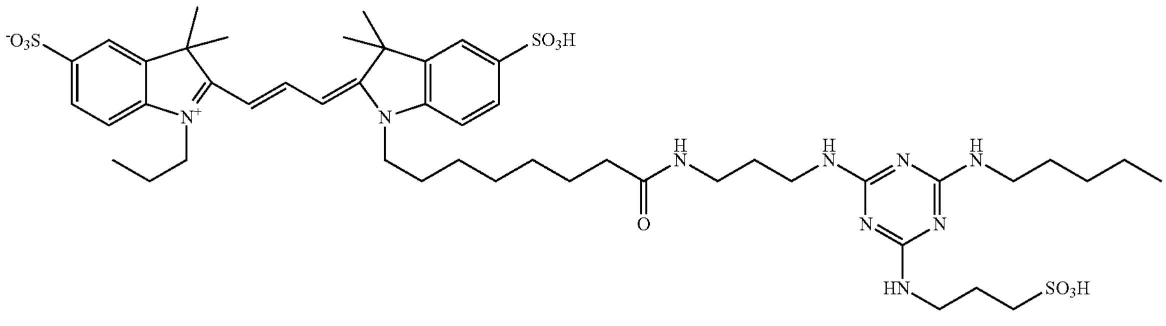

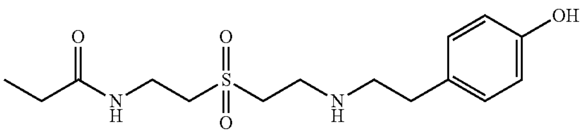

-continued
3
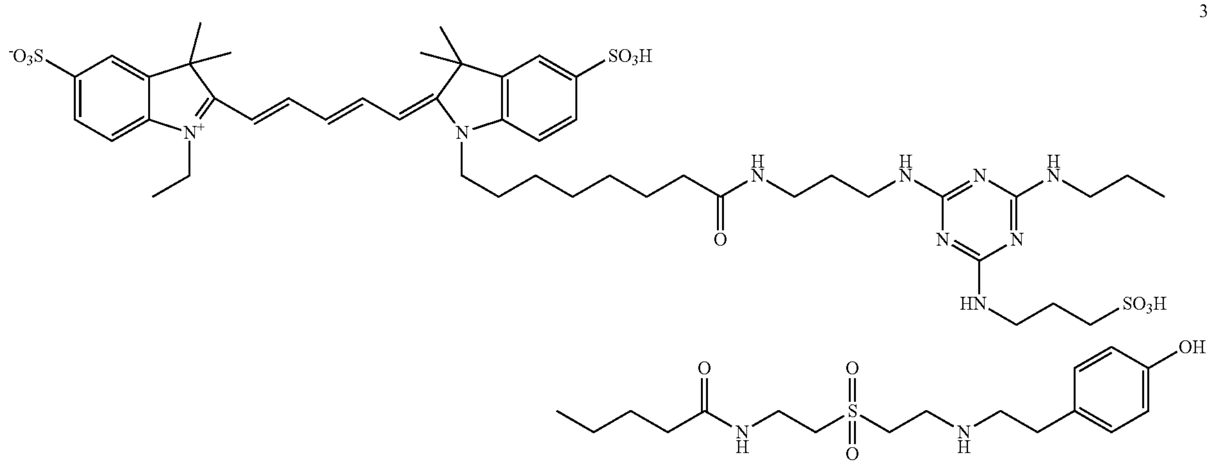
4
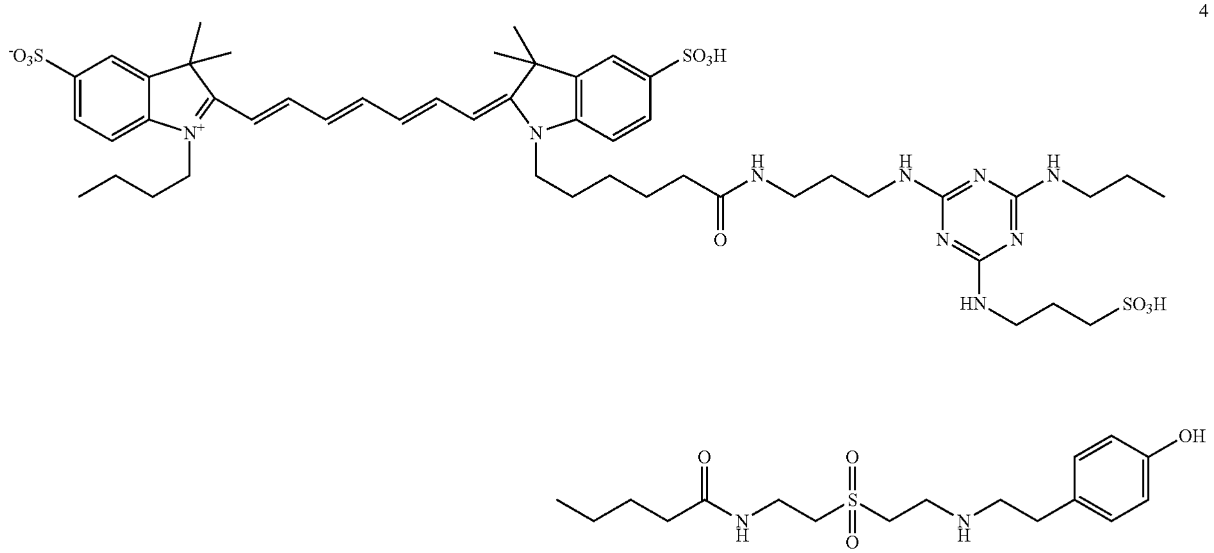
5
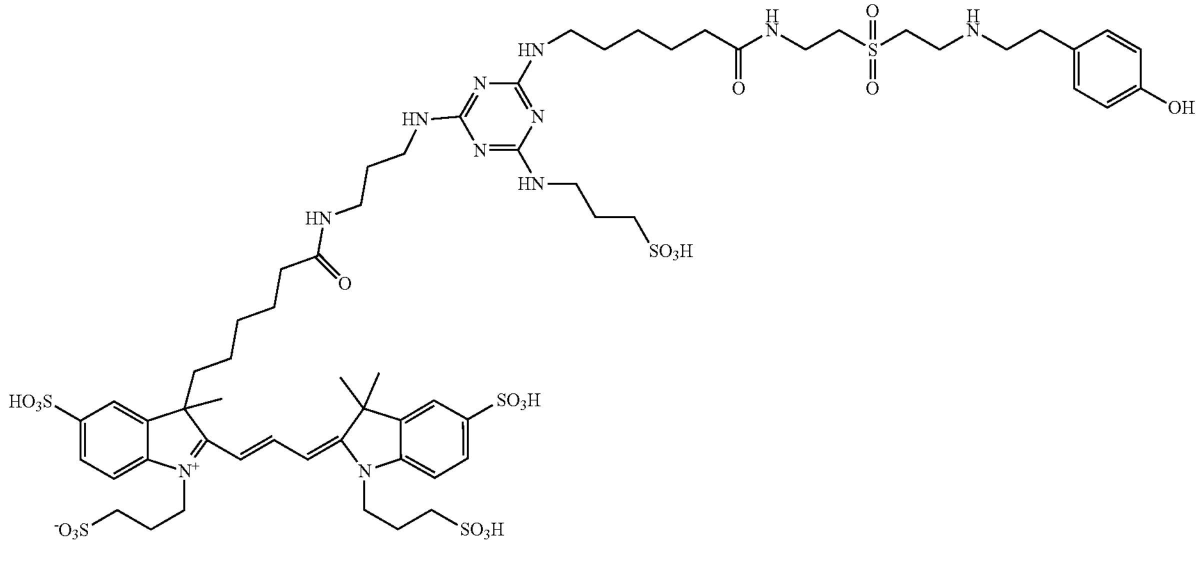

-continued
6
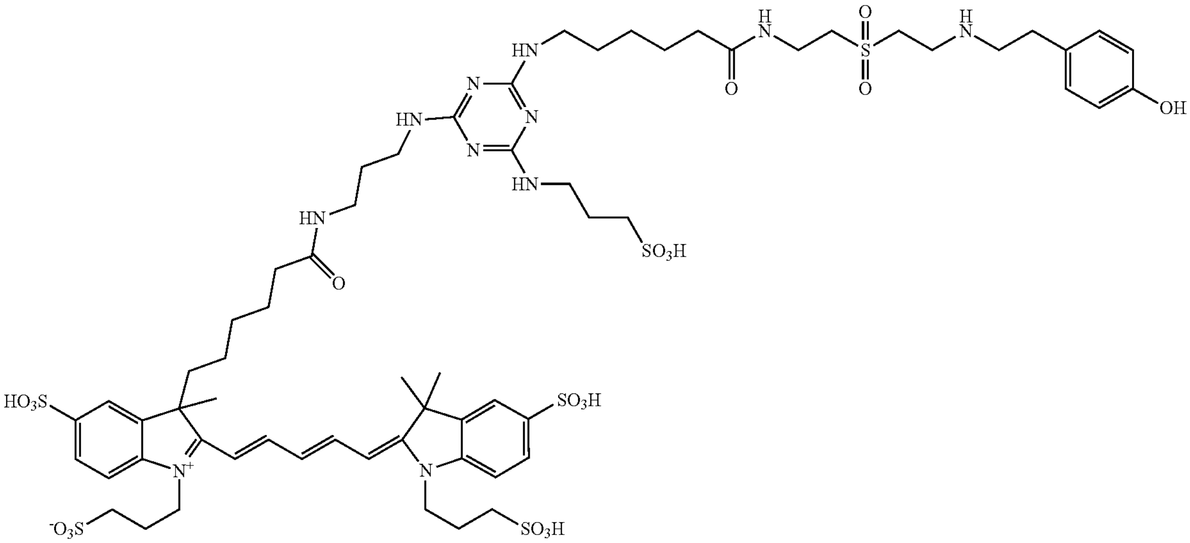
7
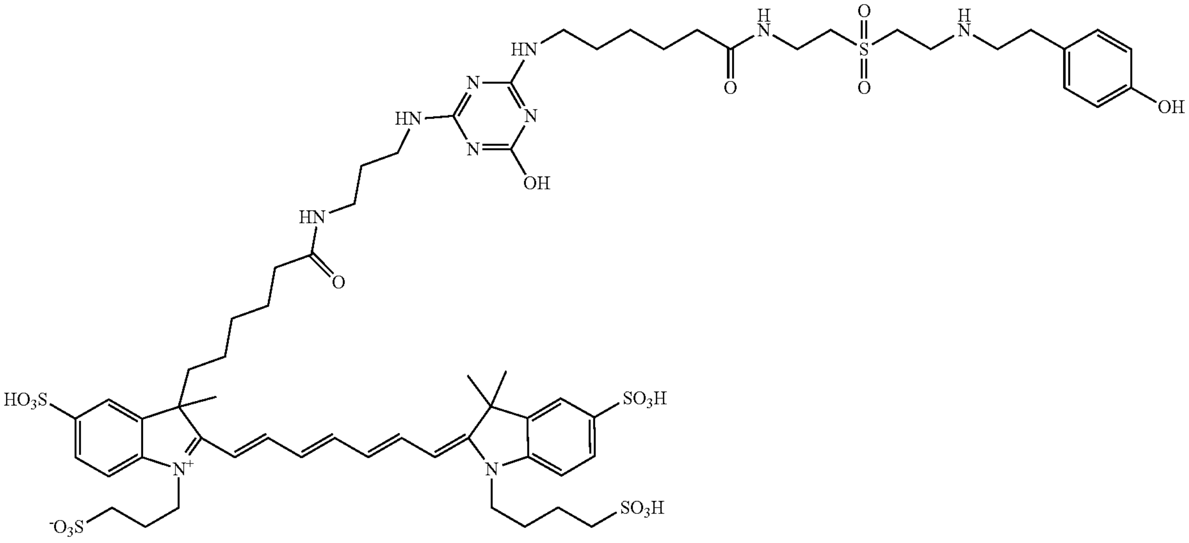
8
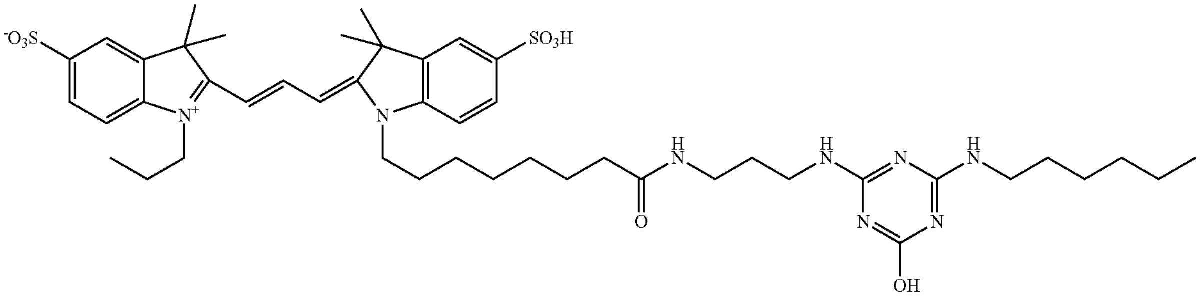
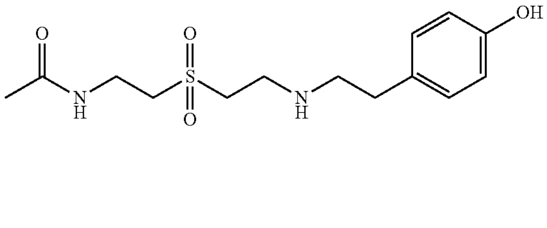

-continued
9
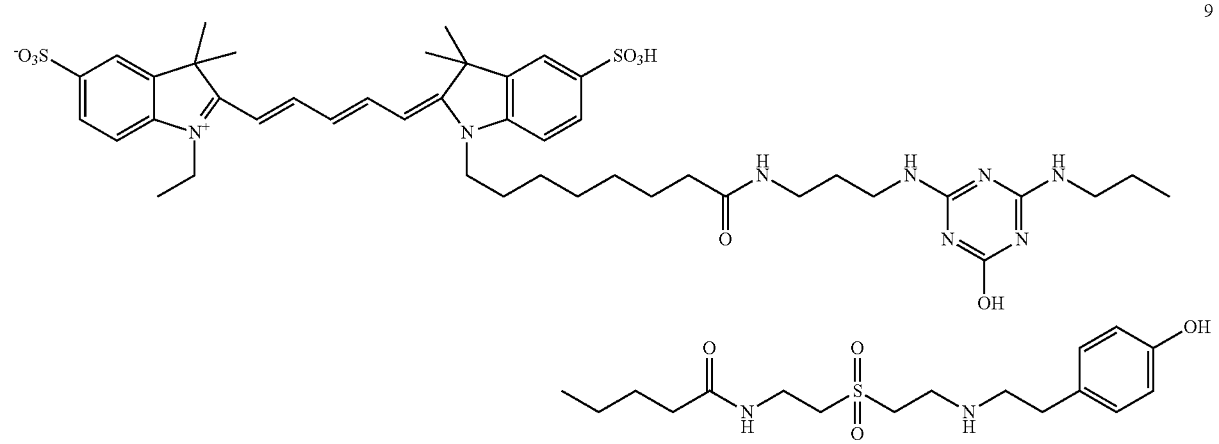
10
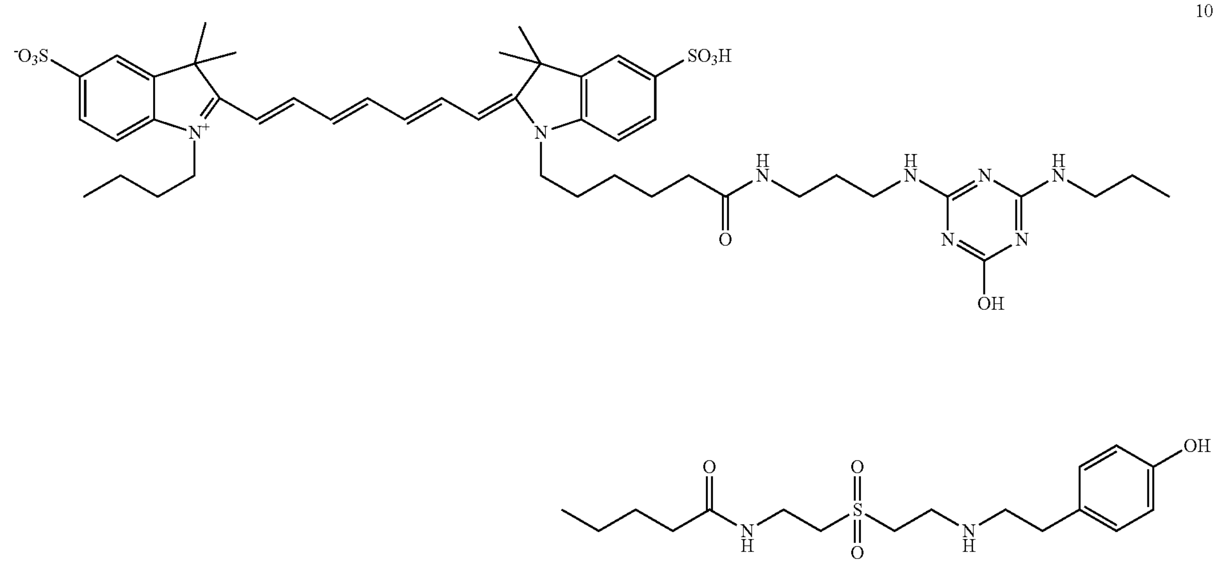
11
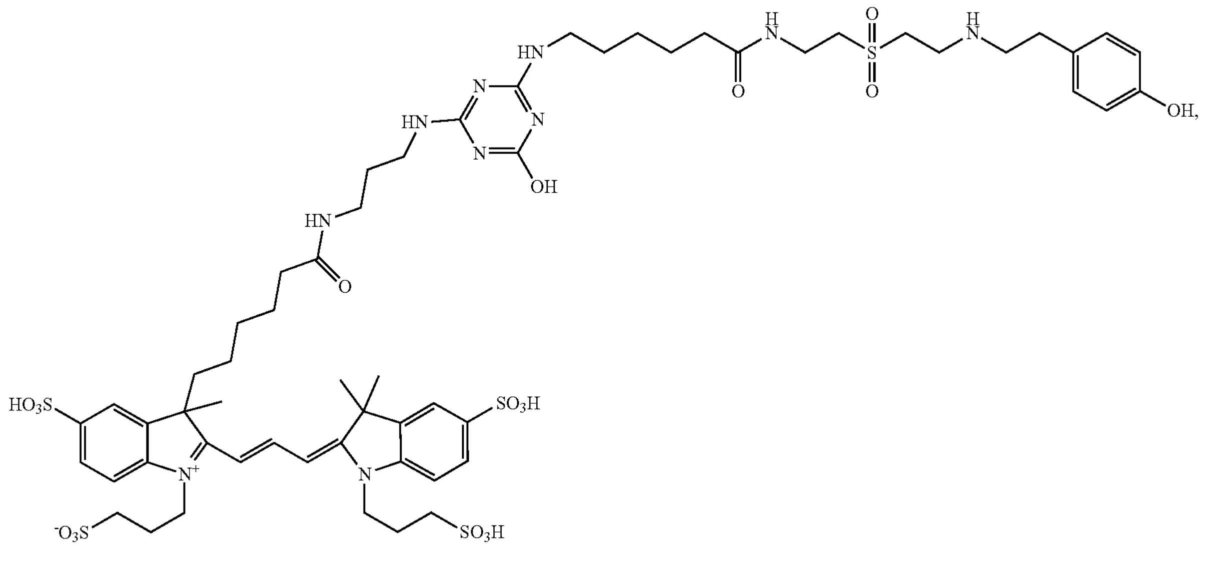

-continued

12

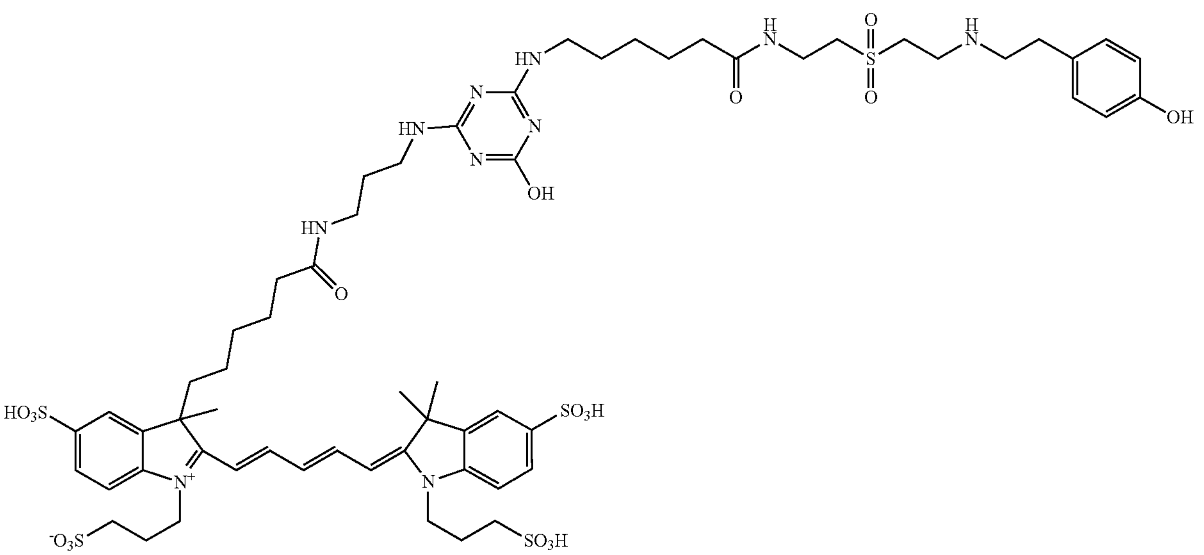

The chemical represented by the formula 1 can be a chemical for immunohistochemistry. The said fluorescent chemical can be a multi-immunohistochemical for staining multiple markers simultaneously.

In another mode in the present invention, it is provided fluorescent composition for immunohistochemistry including the chemical represented by the chemical formula 1.

[Chemical Formula 1]

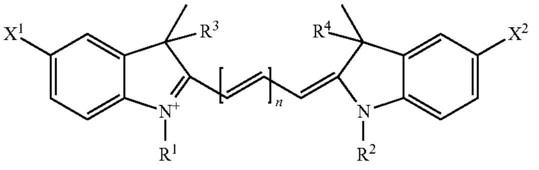

In Chemical Formula 1 above, n is an integer of 1 to 6, $X^1$ and $X^2$ are the same as or different from each other, and each independently selected from H, $-SO_3^-$ and $-SO_3H$, $R^1$ and $R^2$ are the same as each other or each independently selected from $C_{1-7}$ alkyl, substituted or unsubstituted $C_{8-20}$ alkyl, $-(CH_2)_{m1}SO_3^-$, $-(CH_2)_{m2}SO_3H$, and

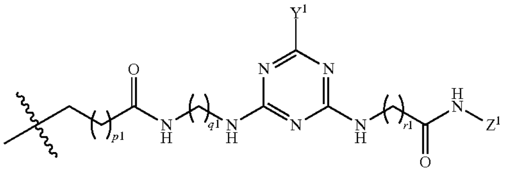

m1 is an integer of 1 to 7, m2 is an integer of 1 to 7, p1 is an integer of 1 to 10, q1 is an integer of 0 to 10, r1 is an integer of 1 to 10, and $Y^1$ is selected from H, —OH, halogen and

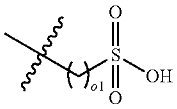

o1 is an integer of 1 to 10, $Z^1$ is selected from H, $C_{1-7}$ alkyl, substituted or unsubstituted $C_{8-20}$ alkyl and

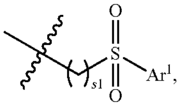

s1 is an integer of 1 to 10, and $Ar^1$ is selected from H, $C_{1-7}$ alkyl, substituted or unsubstituted $C_{8-20}$ alkyl, $C_{1-7}$ aminoalkyl and

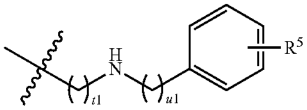

t1 is an integer of 1 to 10, u1 is an integer of 1 to 10, and $R_5$ is selected from H, OH, $C_{1-7}$ alkyl, substituted or unsubstituted $C_{8-20}$ alkyl, and $R^3$ and $R^4$ are the same as or different from each other and each independently selected from substituted or unsubstituted $C_{1-7}$ alkyl, substituted, unsubstituted $C_{8-20}$ alkyl and

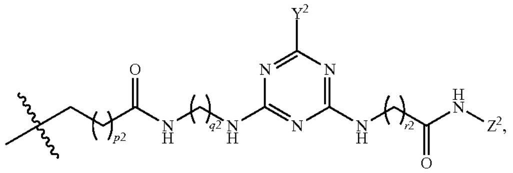

p2 is an integer of 1 to 10, q2 is an integer of 1 to 10, r2 is an integer of 1 to 10, and $Y^2$ is selected from H, —OH, halogen and

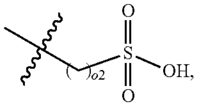

o2 is an integer of 1 to 10, $Z^2$ is selected from H, substituted or unsubstituted $C_{1-7}$ alkyl, substituted or unsubstituted $C_{8-20}$ alkyl and

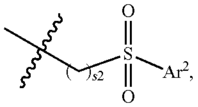

s2 is an integer of 1 to 10, and $Ar^2$ is selected from H, substituted or unsubstituted $C_{1-7}$ alkyl, substituted or unsubstituted $C_{8-20}$ alkyl, $C_{1-7}$ amino-alkyl and

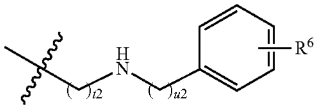

and t2 is an integer of 1 to 10, u2 is an integer of 1 to 10, $R^6$ is selected from H, —OH, substituted or unsubstituted $C_{1-7}$ alkyl and substituted or unsubstituted $C_{8-20}$ alkyl.

More preferably, $R^3$ and $R^4$ are the same as or different from each other and each independently selected from substituted or unsubstituted $C_{1-7}$ alkyl, substituted, unsubstituted $C_{8-20}$ alkyl and

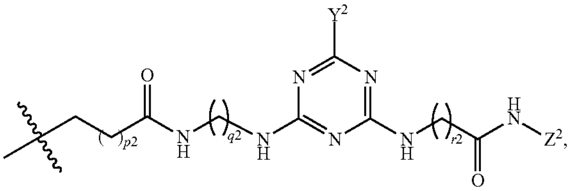

p2 is an integer of 1 to 10, q2 is an integer of 1 to 10, r2 is an integer of 1 to 10, and $Y^2$ is selected from H, —OH, halogen and

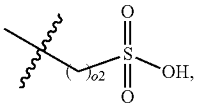

o2 is an integer of 1 to 10, $Z^2$ is selected from H, substituted or unsubstituted $C_{1-7}$ alkyl, substituted or unsubstituted $C_{8-20}$ alkyl and

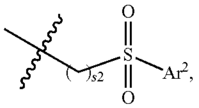

s2 is an integer of 1 to 10, and $Ar^2$ is selected from H, substituted or unsubstituted $C_{1-7}$ alkyl, substituted or unsubstituted $C_{8-20}$ alkyl, $C_{1-7}$ amino-alkyl and

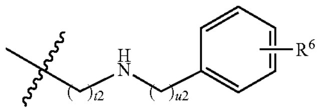

and t2 is an integer of 1 to 10, u2 is an integer of 1 to 10, $R^6$ is selected from H, —OH, substituted or unsubstituted $C_{1-7}$ alkyl and substituted or unsubstituted $C_{8-20}$ alkyl.

BRIEF DESCRIPTION OF THE DRAWINGS

The above and other aspects, features and other advantages of the present invention will be more clearly understood from the following detailed description taken in conjunction with the accompanying drawings, in which:

FIG. 1 shows a fluorescent image from example 1 in accordance with exemplary embodiments of the present invention.

DETAILED DESCRIPTION OF EXEMPLARY EMBODIMENTS

Various modifications can be added in the present invention and the present invention includes a lot of embodiments. In the description only several specific examples are exemplified and described in detail.

However, the present invention is not limited by the above embodiments, and various modifications, changes, equivalents and alternatives which can be made by those skilled in the art within the spirit and scope of the present invention can be included in the present invention. In this description, the explanation about prior arts which may equivocate the substance of the present invention is left out.

The term 'substituted' means that at least one hydrogen atom is substituted by any one of the substituents from the group of deuterium, $C_1$-$C_{10}$ alkyl, $C_1$-$C_{10}$ cycloalkyl, $C_2$ to $C_{10}$ heterocycloalkyl, $C_1$ to $C_{10}$ halogenated alkyl, $C_6$ to $C_{10}$ aryl, $C_1$ to $C_{10}$ heteroaryl, $C_1$ to $C_{10}$ alkoxy, $C_3$ to $C_{10}$ cycloalkoxy, $C_1$ to $C_{10}$ heterocycloalkoxy, $C_2$ to $C_{10}$ alkenyl, $C_2$ to $C_{10}$ alkynyl, $C_6$ to $C_{10}$ aryloxy, $C_1$ to $C_{10}$ heteroaryloxy, Silyloxy(-$OSiH_3$), —$OSiR^1H_2$($R^1$ is $C_1$-$C_{10}$ alkyl or $C_6$ to $C_{10}$ aryl), —$OSiR^1R^2H$ ($R^1$ and $R^2$ are independently $C_1$-$C_{10}$ alkyl or $C_6$ to $C_{10}$ aryl), —$OSiR^1R^2R^3$, ($R^1$, $R^2$ and $R^3$ 는 are independently $C_1$-$C_{10}$ alkyl or $C_6$ to $C_{10}$ aryl), $C_1$ to $C_{10}$ acyl, $C_2$ to $C_{10}$ acyloxy, $C_2$ to $C_{10}$ heteroaryloxy, $C_1$ to $C_{10}$ sulfonyl, $C_1$ to $C_{10}$ alkylthiol, $C_3$ to $C_{10}$ cycloalkylthiol, $C_1$ to $C_{10}$ heterocycloalkylthiol, $C_6$ to $C_{10}$ arylthiol, $C_1$ to $C_{10}$ heteroarylthiol, $C_1$ to $C_{10}$ phosphate amide, silyl ($SiR^1R^2R^3$: $R^1$, $R^2$ and $R^3$ are independently hydrogen atom, $C_1$-$C_{10}$ alkyl or $C_6$ to $C_{10}$ aryl), amine(-NRR', here R and R' are independently hydrogen atom, $C_1$-$C_{10}$ alkyl or $C_6$ to $C_{10}$ aryl), carboxyl, halogen, cyano, nitro, azo and hydroxy. In addition, in the said substituents two substituent in neighbor can form a fused saturated or unsaturated ring.

Additionally, in the said 'saturated or unsaturated $C_1$-$C_{10}$ alkyl' or 'saturated or unsaturated $C_6$-$C_{10}$ aryl', etc, the range of carbon numbers in the alkyl or aryl means the overall number of carbons that comprise the part of alkyl or aryl in view of unsaturated condition without considering the saturated part of the said substituents.

For example, para-substituted butyl means C6 aryl substituted by butyl with 4 carbons.

In this description, the term 'hydrogen' means hydrogen, deuterium or trillium without any definition.

In this description, the term 'alkyl' means aliphatic carbohydrate without any definition.

Alkyl may be 'saturated alkyl' without any double or triple bonds

Alkyl may be a 'unsaturated alkyl' with at least one double or triple bonds.

Alkyl may be branched, unbranched or cyclic alkyl whether or not saturated or unsaturated.

For example, $C_1$ to $C_4$ alkyl may be 1 to 4 carbons in alkyl chain, which is selected from the group of methyl, ethyl, propyl, iso-propyl, n-butyl, iso-butyl, sec-butyl and t-butyl.

More specifically, the said alkyl may mean any one of alkyl selected from the group of methyl, ethyl, propyl, isopropyl, butyl, isobutyl, t-butyl, pentyl, hexyl, ethenyl, propenyl, butenyl, cyclopropyl, cyclobutyl, cyclopentyl, cyclohexyl, etc.

Hereinafter, the fluorescent chemicals in accordance with exemplary embodiments of the present invention are described below.

Exemplary embodiments of the present invention may use a fluorescent compound represented by the following Chemical Formula 1.

[Chemical Formula 1]

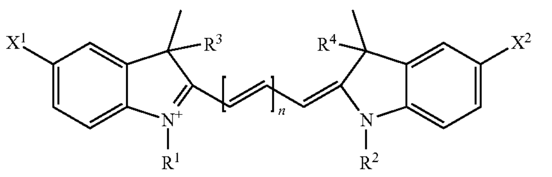

In Chemical Formula 1 above, n is an integer of 1 to 6, $X^1$ and $X^2$ are the same as or different from each other, and each independently selected from H, —$SO_3^-$ and —$SO_3H$, $R^1$ and $R^2$ are the same as each other or each independently selected from $C_{1-7}$ alkyl, substituted or unsubstituted $C_{8-20}$ alkyl, —$(CH_2)_{m1}SO_3^-$, —$(CH_2)_{m2}SO_3H$, and

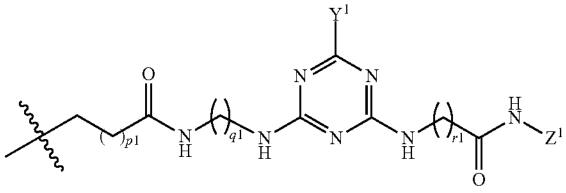

m1 is an integer of 1 to 7, m2 is an integer of 1 to 7, p1 is an integer of 1 to 10, q1 is an integer of 0 to 10, r1 is an integer of 1 to 10, and $Y^1$ is selected from H, —OH, halogen and

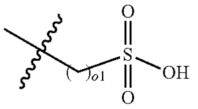

o1 is an integer of 1 to 10, $Z^1$ is selected from H, $C_{1-7}$ alkyl, substituted or unsubstituted $C_{8-20}$ alkyl and

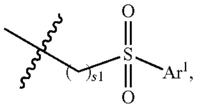

s1 is an integer of 1 to 10, and $Ar^1$ is selected from H, $C_{1-7}$ alkyl, substituted or unsubstituted $C_{8-20}$ alkyl, $C_{1-7}$ aminoalkyl and

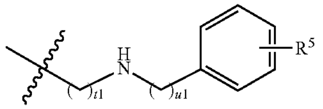

t1 is an integer of 1 to 10, u1 is an integer of 1 to 10, and $R_5$ is selected from H, OH, $C_{1-7}$ alkyl, substituted or unsubstituted $C_{8-20}$ alkyl, and $R^3$ and $R^4$ are the same as or different from each other and each independently selected from substituted or unsubstituted $C_{1-7}$ alkyl, substituted, unsubstituted $C_{8-20}$ alkyl and

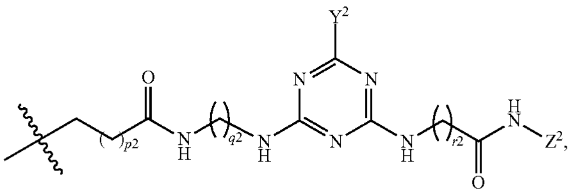

p2 is an integer of 1 to 10, q2 is an integer of 1 to 10, r2 is an integer of 1 to 10, and $Y^2$ is selected from H, —OH, halogen and

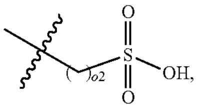

o2 is an integer of 1 to 10, $Z^2$ is selected from H, substituted or unsubstituted $C_{1-7}$ alkyl, substituted or unsubstituted $C_{8-20}$ alkyl and

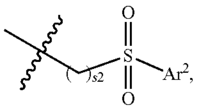

s2 is an integer of 1 to 10, and $Ar^2$ is selected from H, substituted or unsubstituted $C_{1-7}$ alkyl, substituted or unsubstituted $C_{8-20}$ alkyl, $C_{1-7}$ aminoalkyl and

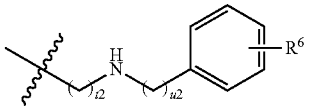

and t2 is an integer of 1 to 10, u2 is an integer of 1 to 10, $R^6$ is selected from H, —OH, substituted or unsubstituted $C_{1-7}$ alkyl and substituted or unsubstituted $C_{8-20}$ alkyl.

Preferably in the chemical formula 1, n is an integer of 1 to 3, $X^1$ and $X^2$ are the same as or different from each other, and each independently selected from —$SO_3^-$ and —$SO_3H$, $R^1$ and $R^2$ are the same as each other or each independently selected from $C_{1-4}$ straight chain alkyl, —$(CH_2)_{m1}SO_3^-$, —$(CH_2)_{m2}SO_3H$, and

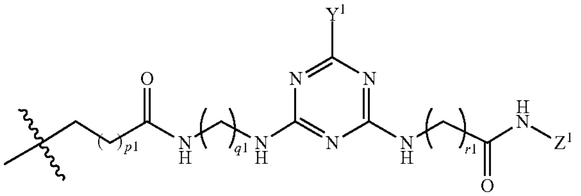

m1 is an integer of 1 to 5, m2 is an integer of 1 to 5, p1 is an integer of 1 to 5, q1 is an integer of 1 to 6, r1 is an integer of 1 to 6, and $Y^1$ is selected from —OH, —$Cl^-$ and

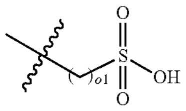

o1 is an integer of 1 to 4, $Z^1$ is selected from H, $C_{1-4}$ straight chain alkyl and

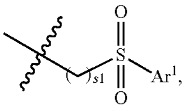

s1 is an integer of 1 to 4, and $Ar^1$ is selected from $C_{1-4}$ straight chain alkyl, $C_{1-4}$ aminoalkyl and

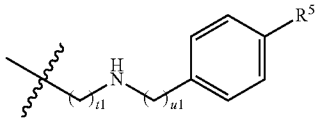

t1 is an integer of 1 to 4, u1 is an integer of 1 to 4, $R^5$ is selected from H, OH, $C_{1-4}$ straight chain alkyl.

More preferably, $R^3$ and $R^4$ are the same as or different from each other and each independently selected from substituted or unsubstituted $C_{1-7}$ alkyl, substituted, unsubstituted $C_{8-20}$ alkyl and

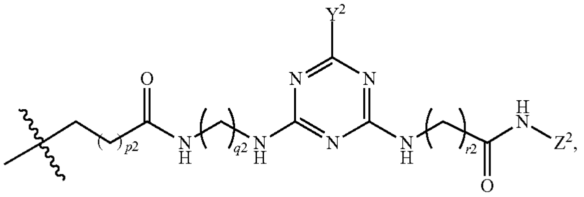

p2 is an integer of 1 to 10, q2 is an integer of 1 to 10, r2 is an integer of 1 to 10, and $Y^2$ is selected from H, —OH, halogen and

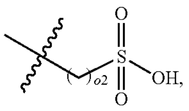

o2 is an integer of 1 to 10, $Z^2$ is selected from H, substituted or unsubstituted $C_{1-7}$ alkyl, substituted or unsubstituted $C_{8-20}$ alkyl and

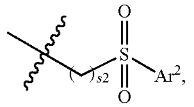

s2 is an integer of 1 to 10, and $Ar^2$ is selected from H, substituted or unsubstituted $C_{1-7}$ alkyl, substituted or unsubstituted $C_{8-20}$ alkyl, $C_{1-7}$ aminoalkyl and

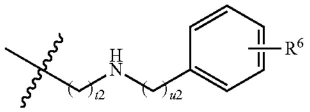

and t2 is an integer of 1 to 10, u2 is an integer of 1 to 10, $R^6$ is selected from H, —OH, substituted or unsubstituted $C_{1-7}$ alkyl and substituted or unsubstituted $C_{8-20}$ alkyl.

More and more preferably in the chemical formula 1, $R^3$ and $R^4$ are the same as or different from each other and each independently selected from $C_{1-4}$ straight chain alkyl and

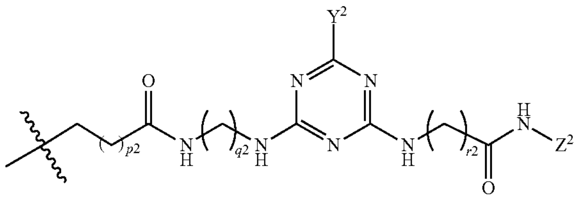

and p2 is an integer of 1 to 5, q2 is an integer of 1 to 5, r2 is an integer of 1 to 6, and $Y^2$ is selected from —OH, —$Cl^-$ and

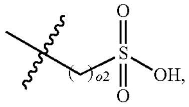

o2 is an integer of 1 to 4, $Z^2$ is selected from H, $C_{1-4}$ straight chain alkyl and

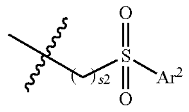

and, s2 is an integer of 1 to 4, and $Ar^2$ is selected from $C_{1-4}$ straight chain alkyl, $C_{1-4}$ aminoalkyl and

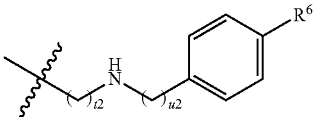

and t2 is an integer of 1 to 4, u2 is an integer of 1 to 6, $R^6$ is selected from H, OH, $C_{1-4}$ straight chain alkyl.

The most preferably, the compound represented by the formula 1 is a compound selected from compounds 1-12 below.

1

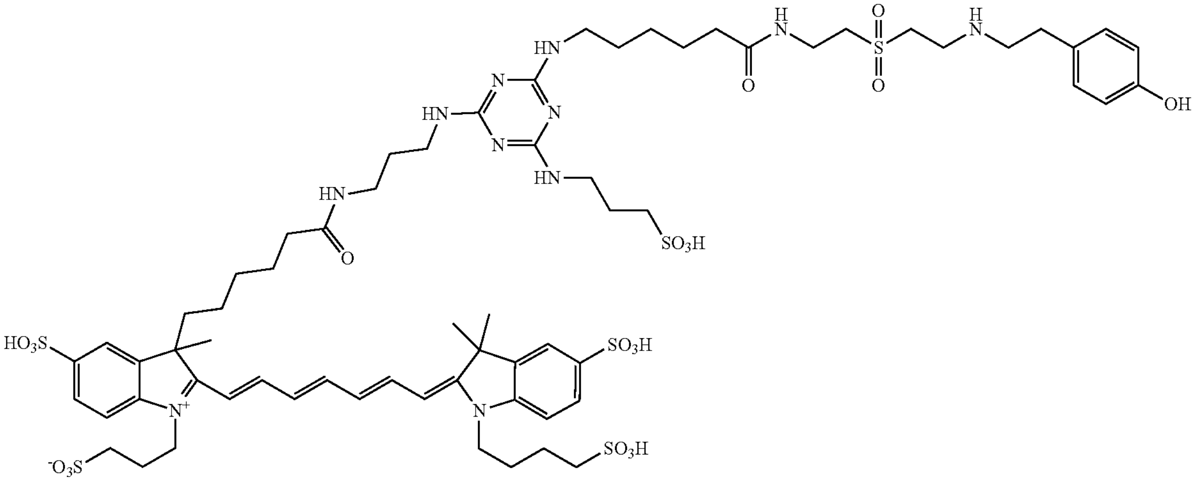

-continued
2
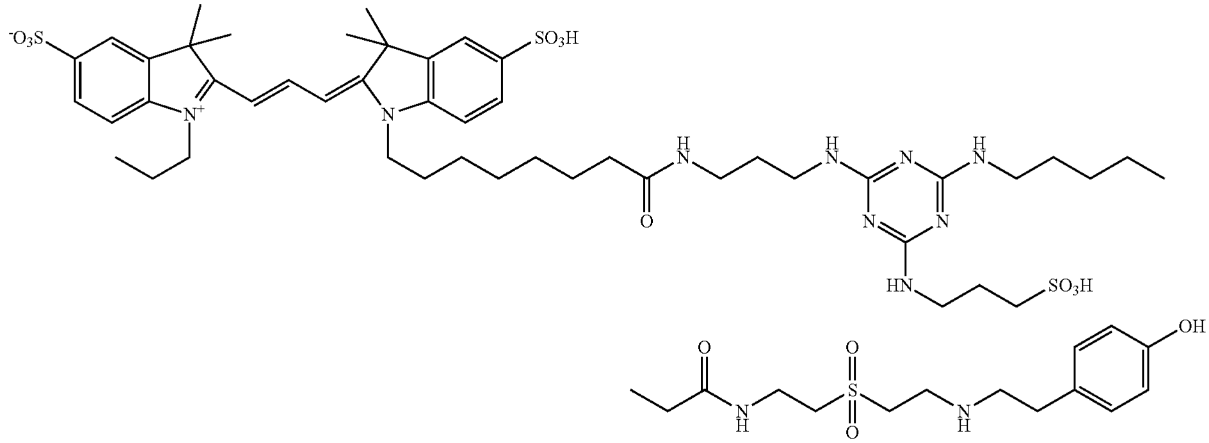
3
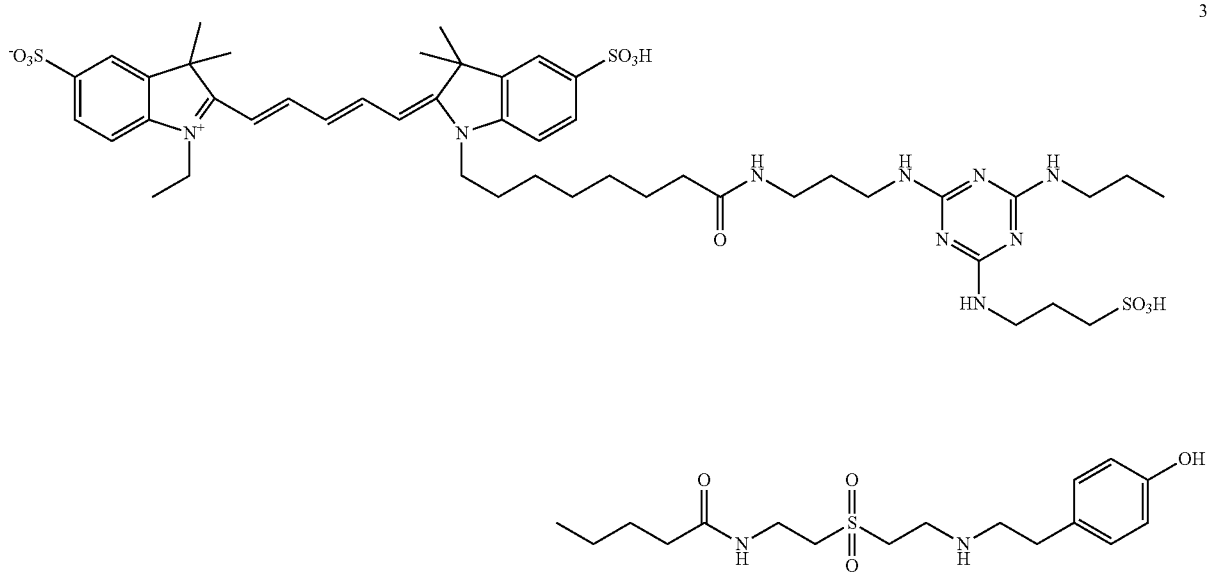
4
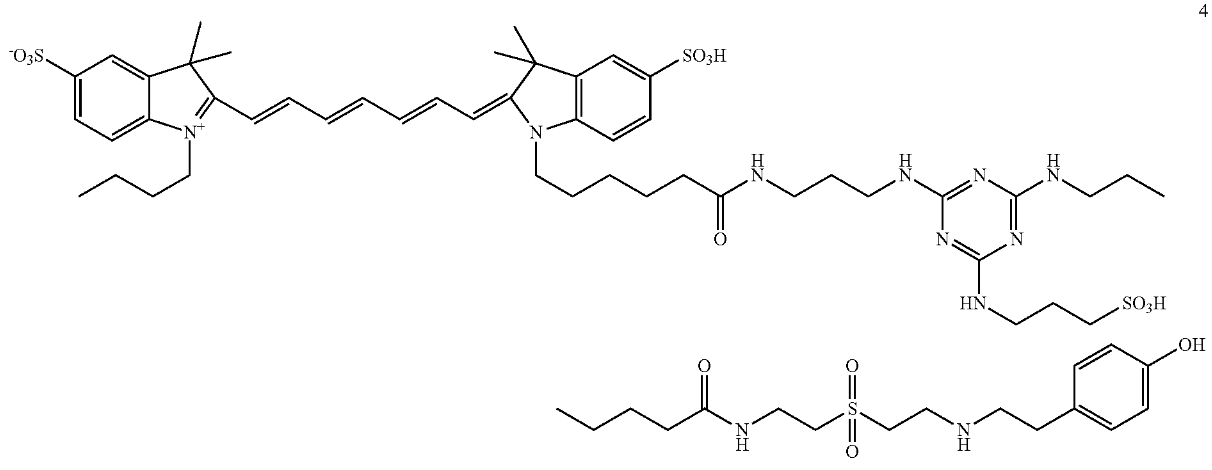

-continued
5
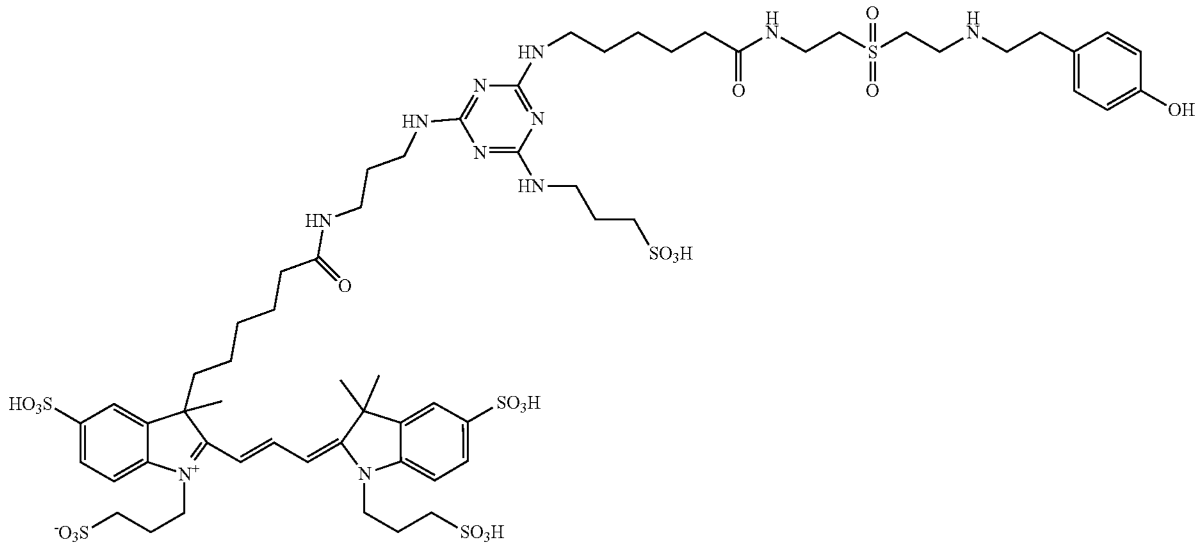
6
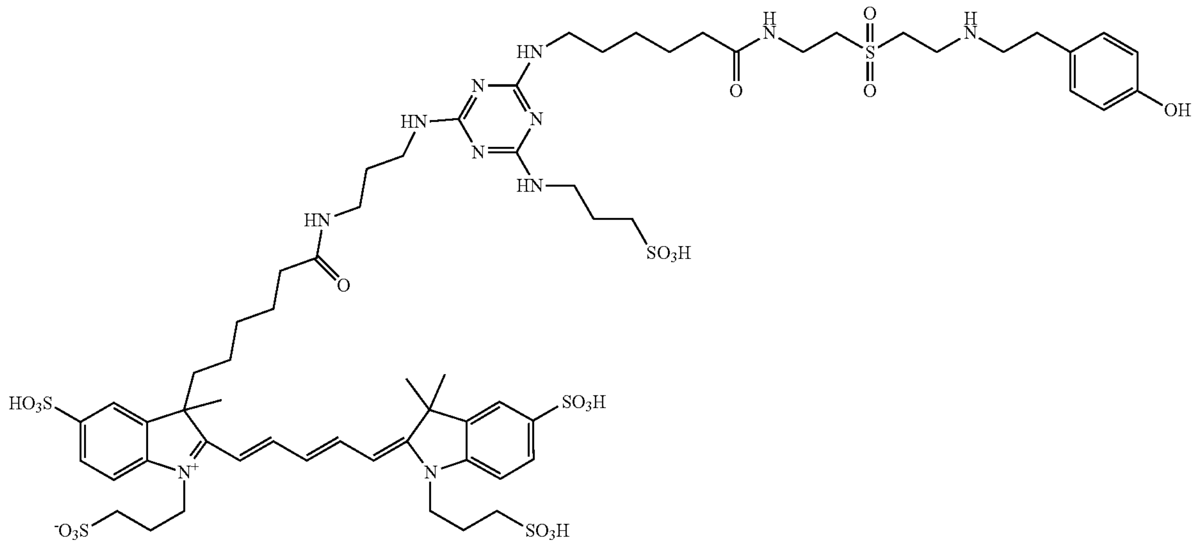

-continued
7
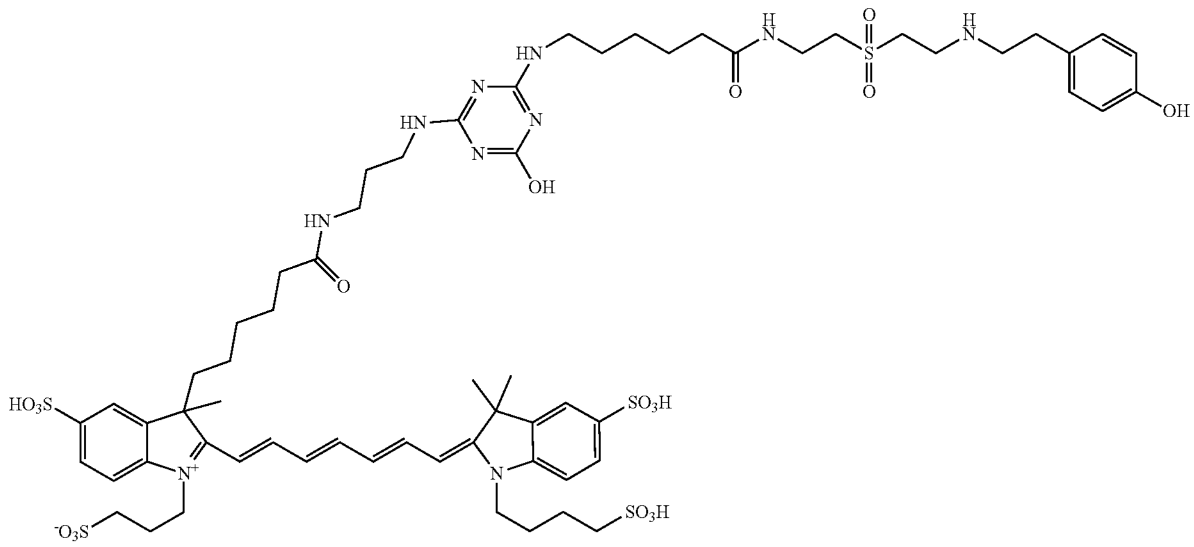
8
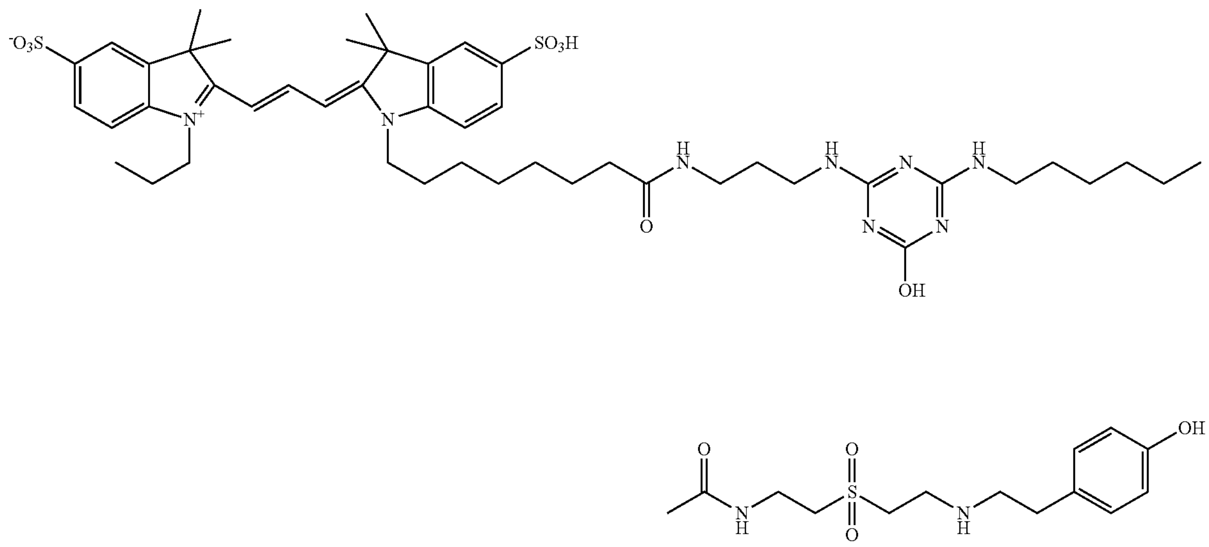
9
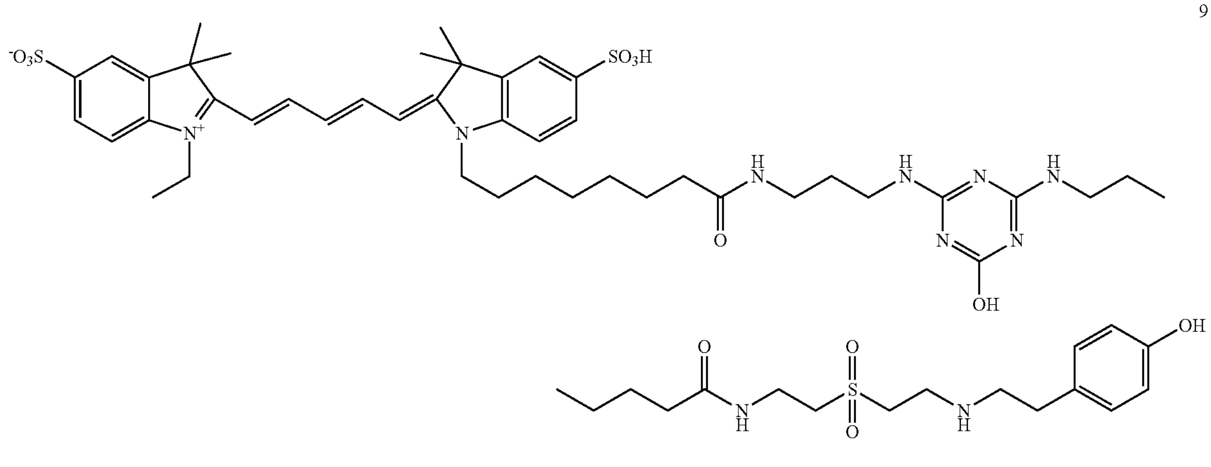

-continued
10
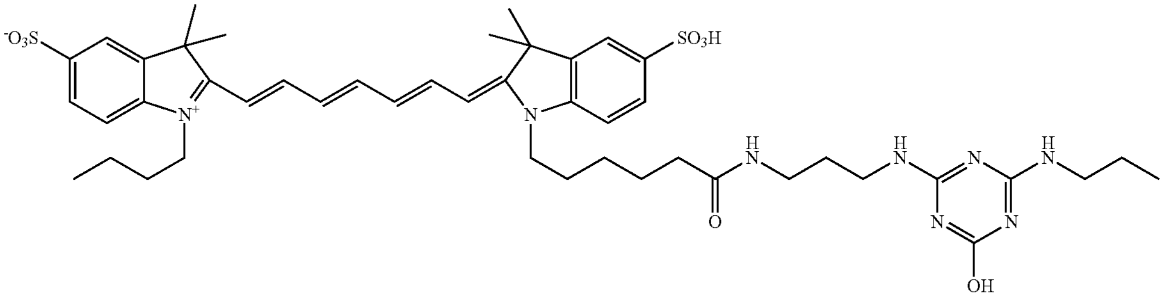
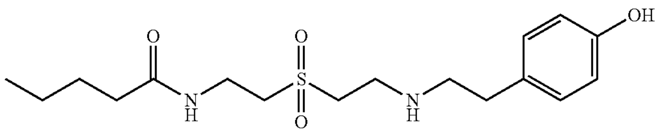
11
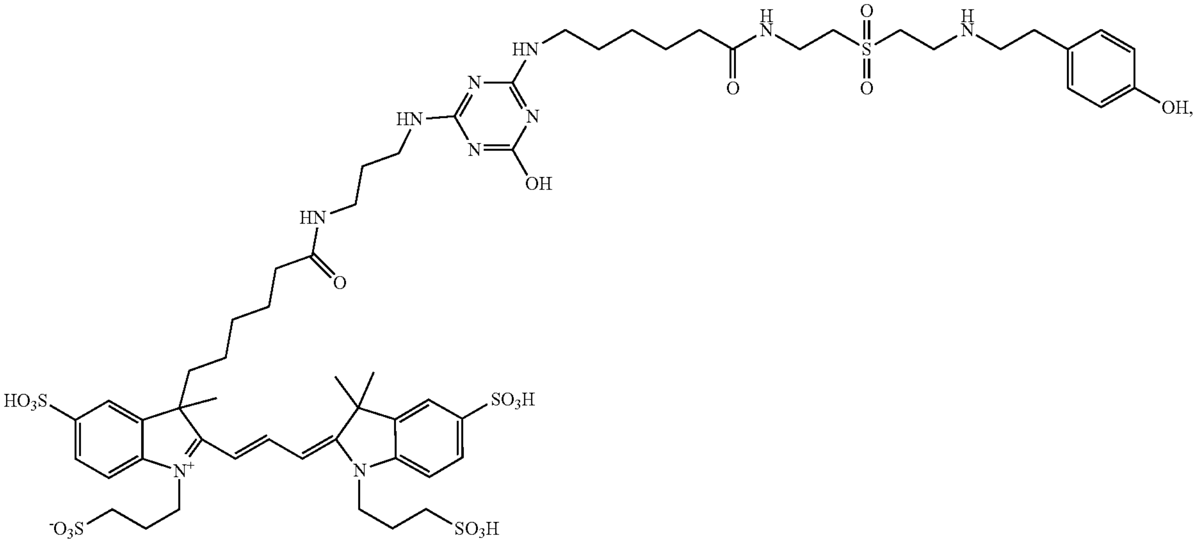
12
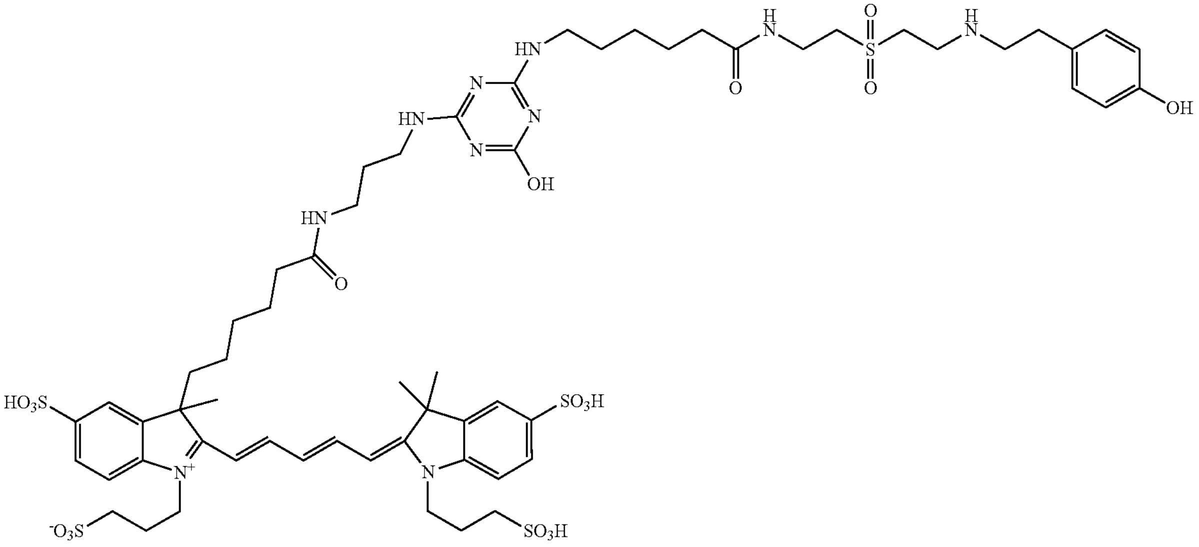

The compound represented by the formula 1 may be a chemical for immunohistochemistry.

The method for labeling the fluorescent compound represented by Chemical Formula 1 is performed by using a buffer selected from the group consisting of a phosphate buffer, a carbonate buffer, and a tris buffer, an organic solvent selected from the group consisting of dimethyl sulfoxide, dimethylformamide, methanol, ethanol and acetonitrile, or water as a solvent and reacting the biomaterial, nanoparticles, or organic compounds with the compound of Chemical Formula 1 at pH 5 to 12. The reaction may be conducted for 30 minutes to 48 hours at a temperature of 20° C. to 80° C.

Most of biomaterials are dissolved in a predetermined buffer from a packaging unit, and in many cases, a separate buffer or pH is required to secure the stability of the biomaterials, and as a result, it is not easy to adjust the buffer or pH with a variable. The compound of Chemical Formula 1 according to exemplary embodiments of the present invention reacts reacting with proteins in various buffers, reaction temperatures, and pH conditions to express fluorescence and thus, is suitable to be used for labeling the biomaterials.

In addition, the present invention provides fluorescent composition for immunohistochemistry including the fluorescent compounds represented by the formula 1. The said formula 1 is explained above.

Hereafter, Examples in accordance with embodiments of the present invention are described.

EXAMPLES

Synthesis of Initial Compound for Preparing Compounds in Accordance with Exemplary Embodiments of Present Invention

Preparing Example 1-1: Synthesis of Compound 1-1

1-1

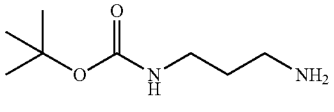

1,3-diaminopropane (20 g, 270 mmol, 7.96 eq) was dissolved in 70 ml of 1,4-dioxane. Di-tert-butyl dicarbonate (7.4 g, 33.9 mmol, 1 eq) was dissolved in 70 ml of 1,4-dioxane and then trickled in a 1,3-diaminopropane solution, and stirred at room temperature day and night and then dried under reduced pressure. The dried material was dissolved in distilled water and then filtered to extract the obtained filtrate with methylene chloride three times. An organic layer obtained after extraction was dried under reduced pressure to obtain a compound 3-1. (6 g, 91.5%)

$R_f$=0.4 (Silicagel, methylene chloride:methanol=8:1)

Preparing Example 1-1: Synthesis of Compound 1-2

1-2

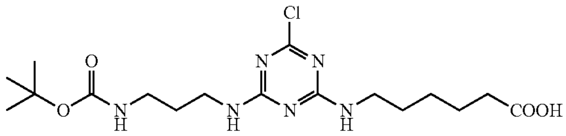

A compound 1-1 (5.1 g, 29.27 mmol, 1 eq) was dissolved in a mixed solution of 150 ml of acetone and 50 ml of distilled water and then stored at 4° C. or less. Cyanuric chloride (CNC) (5.4 g, 29.27 mmol, 1 eq) was fully dissolved in 150 ml of acetone and then added with 50 g of ice and dispersed at 4° C. or less. The compound 1-1 solution was trickled in a CNC solution, and then trickled in an aqueous solution of sodium hydrogencarbonate (fully dissolving 2.46 g carbonate in 50 ml of distilled water) and then, the reaction was performed at 4° C. or less for 2 hours. 6-aminohexanoic acid (1.42 g, 29.27 mmol, 1 eq) was dissolved in 50 ml of distilled water and then trickled in the reaction solution. The aqueous solution of sodium hydrogencarbonate was trickled and the reaction was performed at room temperature for 2 hours and then stirred at 40° C. day and night. The reaction solution was dried under reduced pressure and purified using silica gel chromatography to obtain a compound 1-2. (9 g, 73.8%)

$R_f$=0.7 (Silicagel, methylene chloride:methanol=8:1)

LC/MS, calculated value of $C_{17}H_{29}ClN_6O_4$ 416.91, measured value of 415.2

Preparing Example 1-3: Synthesis of Compound 1-3

1-3

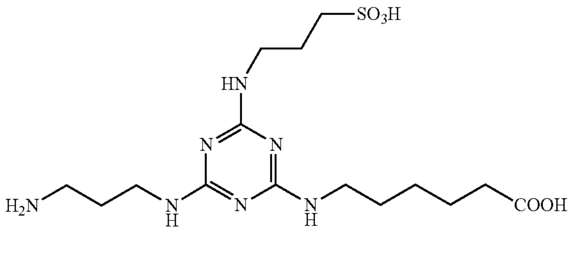

The compound 1-2 (4 g, 9.61 mmol, 1 eq) and 3-Amino-1-propanesulfonic acid) (1.6 g, 11.53 mmol, 1.2 eq) were fully dissolved in 6.7 ml of imethylformamide (DMF) and then added with 40 ml of distilled water. Thereafter 2 ml of 30% sodium hydroxide was added and then stirred in 4 hours at 100° C. and the reaction-solution was lyophilized.

Thereafter, 40 ml of a 6 N aqueous hydrochloric acid solution was added, and then the reaction solution was proceeded in 2 hours at room temperature. The reaction solution was lyophilized and subjected to a reverse phase column to obtain a compound 1-3. (1.6 g, 40%)

$R_f$=0.23 (Silicagel, methylene chloride:methanol=8:1)

LC/MS, calculated value of $C_{15}H_{29}N_7O_5S$ 298.35, measured value of 419.50

Preparing Example 1-4: Synthesis of Compound 1-4

1-4

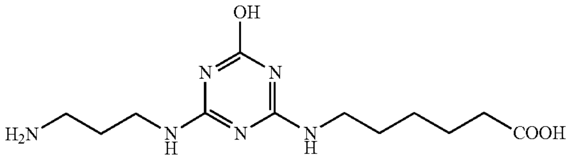

The compound 1-2 (5.1 g, 29.27 mmol, 1 eq) was fully dissolved in 40 ml Acetonitrile(ACN) and 40 ml distilled water was added.

Thereafter, 20 ml of a 6 N aqueous hydrochloric acid solution was added, and then the reaction solution was lyophilized and subjected to a reverse phase column to obtain a compound 1-4. (1.5 g, 69.8%)

$R_f$=0.4 (Silicagel, methylene chloride:methanol=8:1)

LC/MS, calculated value of $C_{12}H_{22}N_6O_3$ 298.35, measured value of 297.3

Preparing Example 1-5: Synthesis of Compound 1-5

1-5

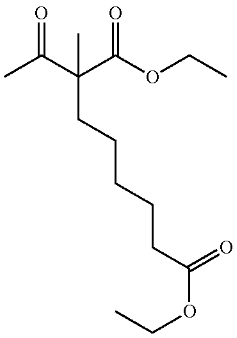

Ethyl 2-methyl acetoacetate (29.2 ml, 0.203 mol, 1 eq), a 21% sodium ethoride solution (64 ml, 0.816 mol, 4 eq), ethyl 6-bromohexanoate (34 ml, 0.192 mol, 1 eq), and ethanol (200 ml) were added and then refluxed at 120° C. for 12 hours. Thereafter, the solvent was extracted by neutralizing pH using 1 M hydrochloric acid and then using chloroform and distilled water. The extracted solvent was dried under reduced pressure and purified using normal chromatography to obtain a compound 4-1. (36.8 g, 63.4%)

$R_f$=0.34 (Silicagel, Hexane/ethyl acetate=10:1 v/v)

Preparing Example 1-6: Synthesis of Compound 1-6

1-6

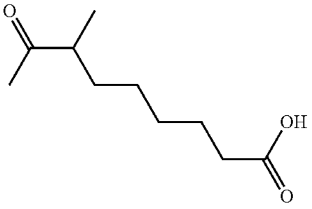

Sodium hydroxide (6.2 g, 0.170 mol, 3.5 eq), methanol (47.2 ml), and distilled water (15.6 ml) were added to the compound 1-5 (13.7 g, 0.0486 mol, 1 eq) and then refluxed at 50° C. for 12 hours. Thereafter, the solvent was dried under reduced pressure and then extracted by adjusting pH to 1 using 1 M hydrochloric acid and using ethyl acetate, and then dried under reduced pressure to obtain a compound 1-6. (8.17 g, 90.7%)

$R_f$=0.05 (Silicagel, Hexane/ethyl acetate=10:1 v/v)

Preparing Example 1-7: Synthesis of Compound 1-7

1-7

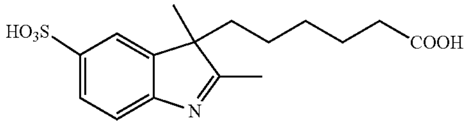

p-hydrazinobenzensulfonic acid hemihydrate (8.25 g, 0.0438 mol, 1 eq) and acetic acid were added to the compound 1-6 (8.165 g, 0.0438 mol, 1 eq) and then refluxed at 120° C. for 5 hours. The mixture was dried under reduced pressure and then purified using normal chromatography and dried under reduced pressure to obtain a compound 1-7. (12.6 g, 84.8%)

$R_f$=0.51 (Silicagel, isobutanol/n-propanol/ethyl acetate/water 2:4:1:3 v/v/v/v)

Preparing Example 1-8: Synthesis of Compound 1-8

1-8

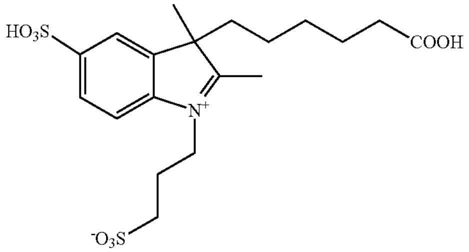

Sodium acetic acid (4.16 g, 0.061 mol, 1.65 eq), 1,3-propane sultone (21.3 ml, 0.243 mol, 6.57 eq), and acetonitrile (24.8 ml) were added to the compound 1-7 (12.57 g, 0.037 mol, 1 eq) and then refluxed at 110° C. for 5 hours. Thereafter, the mixture was dried under reduced pressure and then purified using reverse phase chromatography and dried under reduced pressure to obtain a compound 4-4. (12 g, 70.6%)

$R_f$=0.3 (Silicagel, isobutanol/n-propanol/ethyl acetate/water 2:4:1:3 v/v/v/v)

Preparing Example 1-9: Synthesis of Compound 1-9

1-9

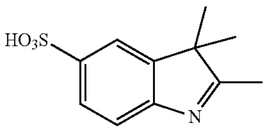

p-Hydrazonibenzene Sulfonic Acid (100 g, 0.53 mol, 1 eq) was added into the mixture of 3-methyl-2-butanone (170 ml, 0.53 mol, 3 eq) and acetic acid and then refluxed in 4 hours at 120° C. Thereafter the mixture was extracted by ethyl acetate amd dried (113 g, 89.2%).

$R_f$=0.58 (isobutanol/n-propanol/ethyl acetate/water 2:4:1:3 v/v/v/v)

Preparing Example 1-10: Synthesis of Compound 1-10

1-10

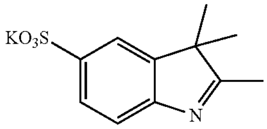

The compound 1-9 (87.9 g, 0.367 mol, 1 eq) was added into the mixture of potassium hydroxide (25.8 g, 0.367 mol, 1 eq), methanol (744 ml) and propanol (832 ml) and the mixtures was reacted in 24 hours at room temperature. Thereafter the mixture was filtered and dried (75 g, 73.8%).

$R_f$=0.58 (isobutanol/n-propanol/ethyl acetate/water 2:4:1:3 v/v/v/v)

Preparing Example 1-11: Synthesis of Compound 1-11

1-11

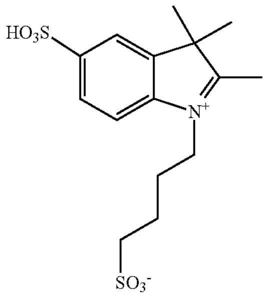

Sodium acetate (17.87 g, 0.216 mol, 1.2 eq), 1,3-propane sultone (70.5 ml, 0.8 mol, 4.5 eq), and acetonitrile (42 ml) were added to the compound 1-10 (50 g, 0.18 mol, 1 eq). Thereafter, the mixture was refluxed at 110° C. for 12 hours and then particles were captured using ethyl acetate and dried (61 g, 94%).

$R_f$=0.3 (isobutanol/n-propanol/ethyl acetate/water 2:4:1:3 v/v/v/v)

Preparing Example 1-12: Synthesis of Compound 1-12

1-12

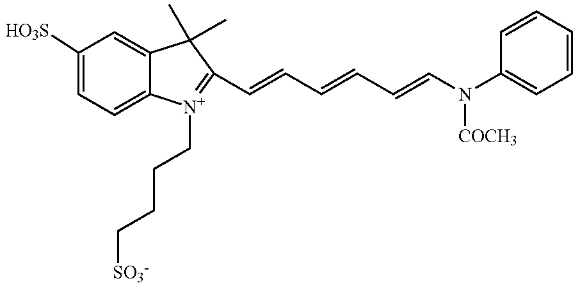

The compound 1-11 (60 g, 0.166 mol, 1 eq) was added into the mixture of glutaconaldehydedianil hydrochloride (42.9 g, 0.166 mol, 1 eq), triethylamine (2.3 ml, 0.016 mol, 0.1 eq) and acetic acid (551 ml) and the mixture was refluxed at 140° C. while heating. Thereafter the particles were extracted using ethyl acetate and dried. The particles were purified using normal chromatography and dried under reduced pressure to obtain a compound 1-12. (7.5 g, 8.5%)

$R_f$=0.59 (Silicagel, isobutanol/n-propanol/ethyl acetate/water 2:4:1:3 v/v/v/v)

Preparing Example 1-13: Synthesis of Compound 1-13

The compound 1-8 (6.5 g, 0.014 mol, 1 eq) and the compound 1-12 (7.5 g, 0.014 mol, 1 eq) were added into the solution of triethylamine (16.6 ml, 0.12 mol, 8.5 eq), acetic anhydride (7.3 ml) and DMF (75 ml) and reacted for 1 hour at room temperature. Thereafter the particles were extracted using ethyl acetate and dried. The particles were purified using normal chromatography and dried under reduced pressure to obtain a compound 1-13. (250 mg, 2%)

$R_f$=0.13 (Silicagel, isobutanol/n-propanol/ethyl acetate/water 2:4:1:3 v/v/v/v)

LC/MS, calculated value of $C_{39}H_{50}N_2O_{14}S_4$ 898.21, measured value of 897.8

Preparing Example 1-14: Synthesis of Compound 1-14

1-14

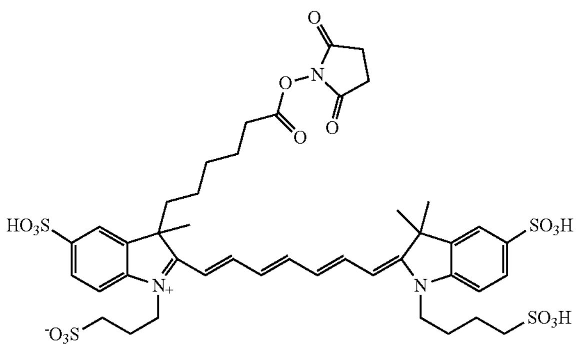

The compound 1-13 (100 mg, 0.111 mmol, 1 eq), TSTU (101 mg, 0.333 mmol, 3 eq) and triethylamine (77.4 ul, 0.555 mmol, 5 eq) were added to 10 mL of DMF and reacted at room temperature for 1 hour. Thereafter particles were generated by adding ether and the particles were filter and dried. The compound 1-14 was obtained (110 mg, 100%).

$R_f$=0.2 (Silicagel, isobutanol/n-propanol/ethyl acetate/water 2:4:1:3 v/v/v/v)

LC/MS, calculated value of $C_{43}H_{53}N_3O_{16}S_4$ 995.23, measured value of 994.3

Preparing Example 1-15: Synthesis of Compound 1-15

1-15

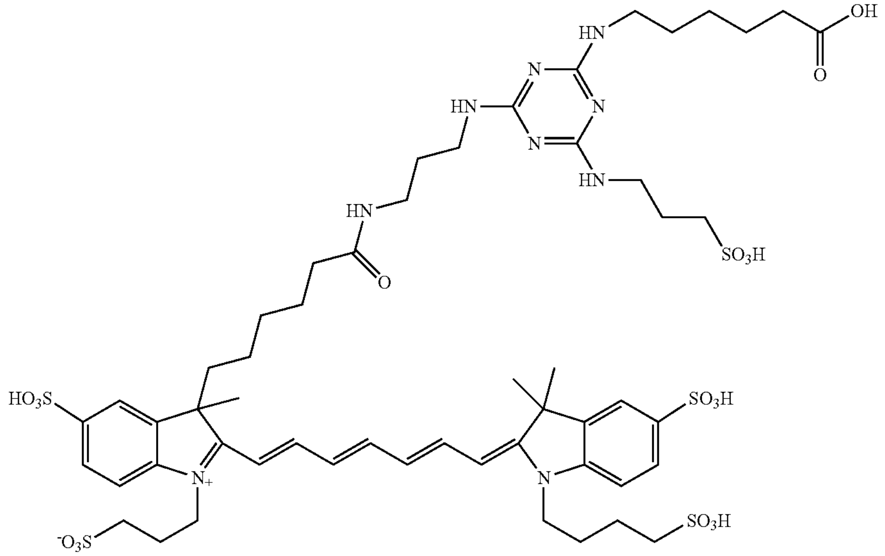

The compound 1-14 (110 mg, 0.111 mmol, 1 eq) and the compound 1-3 (140 mg, 0.333 mmol, 3 eq) were fully dissolved in 10 ml DMF and then Wheeinig base (97 ul, 0.555 mmol, 5 eq) were added. Thereafter the solution was stirred during day and night at room temperature.

After the reaction was confirmed, particles were produced by adding ether and filtered and dried. The obtained material was purified using reverse phase chromatography and then dried under reduced pressure to obtain a compound 1-15. (45 mg, 31.3%)

$R_f$=0.13 (Silicagel, isobutanol/n-propanol/ethyl acetate/water 2:4:1:3 v/v/v/v)

LC/MS, calculated value of $C_{54}H_{77}N_9O_{18}S_5$ 1299.40, measured value of 1297.9

Preparing Example 1-16: Synthesis of Compound 1-16

1-16

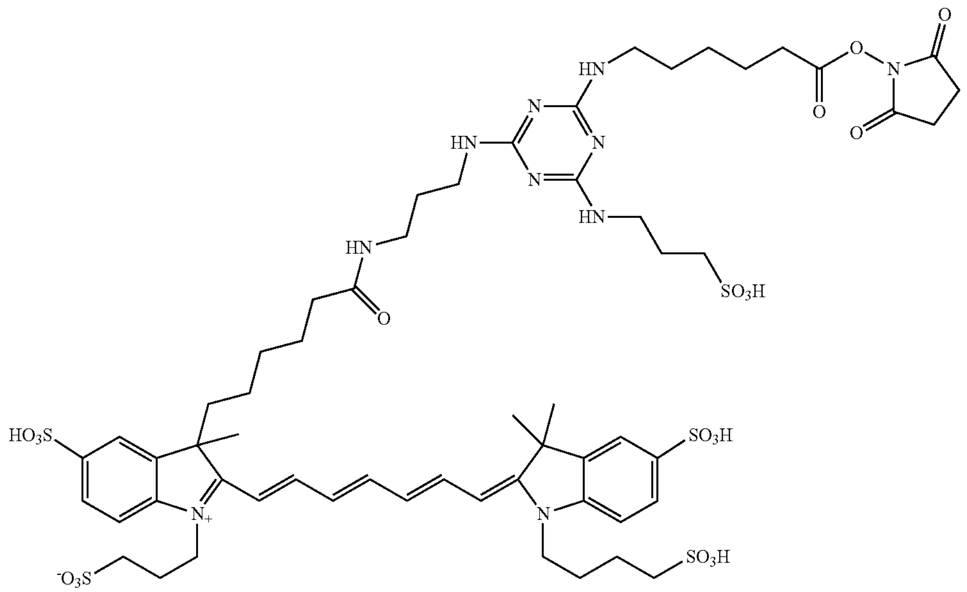

The compound 1-15 (45 mg, 0.035 mmol, 1 eq), TSTU (31.3 mg, 0.104 mmol, 3 eq) and triethylamine (24.4 ul, 0.175 mmol, 5 eq) were added in 5 ml of DMF and then reacted in 1 hour at room temperature. After the reaction was confirmed, particles produced by adding ether were filtered and dried under reduced pressure to obtain a compound 1-16. (45 mg, 100%)

$R_f$=0.18 (Silicagel, isobutanol/n-propanol/ethyl acetate/water 2:4:1:3 v/v/v/v)

LC/MS, calculated value of $C_{58}H_{80}N_{10}O_{20}S_5$ 1396.42, measured value of 1395.3

Preparing Example 1-17: Synthesis of Compound 1-17

1-17

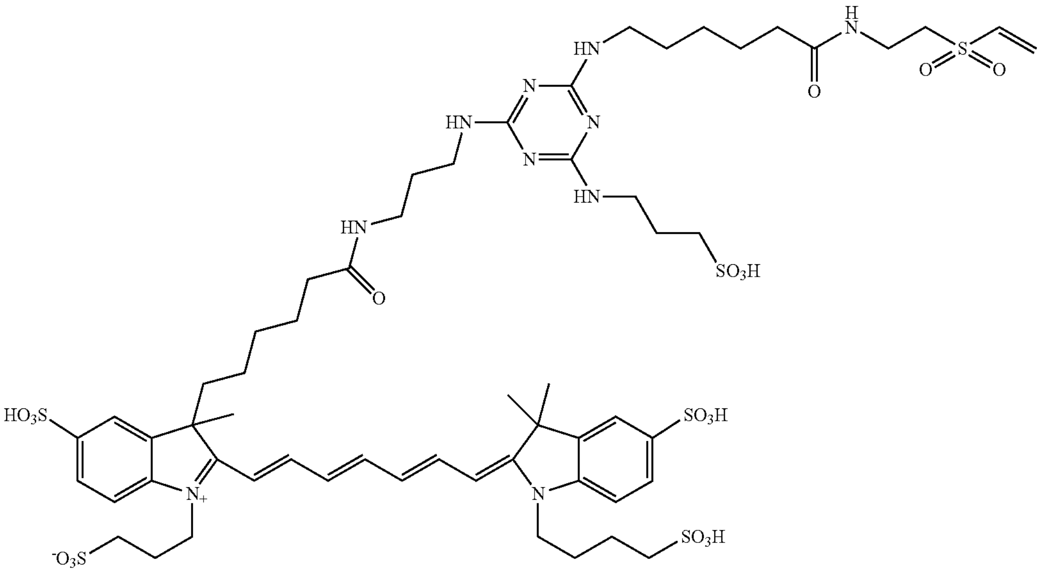

The compound 1-16 (100 mg, 0.077 mmol, 1 eq), 2-(2'-chloroethylsulfonyl)ethylamine salt (32 mg, 0.154 mmol, 2 eq) and Wheeinig base (67 ul, 0.385 mmol, 5 eq) were added into 10 ml DMF and reacted in 12 hours at room temperature. The solid particles produced were captured by diethylether and the particles were dried under reduced pressure. Thereafter the particles were purified using reverse phase chromatography by acetonitrile as developer to obtain the chemical 1-17 (33 mg, 30.3%).

$R_f$=0.24 (Silicagel, isobutanol/n-propanol/ethyl acetate/water 2:4:1:3 v/v/v/v)

LC/MS, calculated value of $C_{58}H_{84}N_{10}O_{19}S_6$ 1416.42, measured value of 1417.5

Example 1: Synthesis of Chemical 1 in Accordance with Exemplary Embodiments of the Present Invention

1

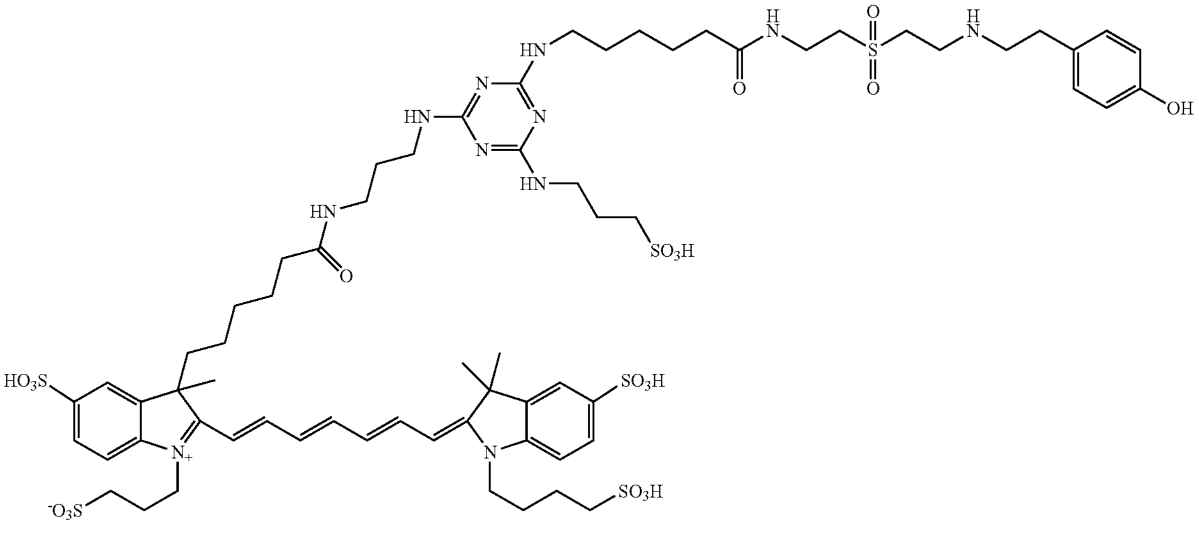

The compound 1-13 (33 mg, 0.023 mmol, 1 eq), tyramine (6.4 mg, 0.047 mmol, 2 eq) and triethylamine (8.2 ul, 0.047 mmol, 2 eq) were added into 3 ml DMF and reacted for 12 hours at room temperature. The solid particles produced were captured by diethylether and the particles were dried under reduced pressure. Thereafter the particles were purified using reverse phase chromatography by acetonitrile as developer to obtain the compound 1 (12.11 mg, 33.9%). $R_f$=0.29 (Silicagel, isobutanol/n-propanol/ethyl acetate/water 2:4:1:3 v/v/v/v)

LC/MS, calculated value of $C_{66}H_{95}N_{11}O_{20}S_6$ 1553.51, measured value of 1552.8

Example 2: Synthesis of Chemical 2 in Accordance with Exemplary Embodiments of the Present Invention

2

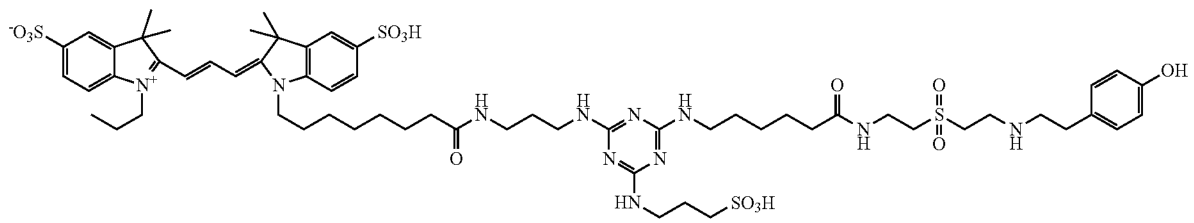

The compound 2 was obtained by applying the method described in example 1 excepting using Flamma 552 Carboxylic acid (BioActs) instead of the compound 1-13 in example 1 (113 mg, 64.4%).

$R_f$=0.28 (Silicagel, isobutanol/n-propanol/ethyl acetate/water 2:4:1:3 v/v/v/v)

LC/MS, calculated value of $C_{61}H_{89}N_{11}O_{14}S_4$ 1327.55, measured value of 1326.1

Example 3: Synthesis of Compound 3 in Accordance with Exemplary Embodiments of the Present Invention

3

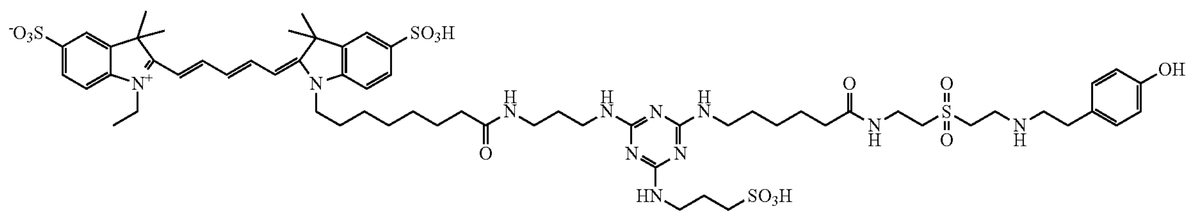

The compound 3 was obtained by applying the method described in example 1 except using Flamma 648 Carboxylic acid (BioActs) instead of the compound 1-13 in example 1 (138 mg, 53.4%).

$R_f$=0.27 (Silicagel, isobutanol/n-propanol/ethyl acetate/water 2:4:1:3 v/v/v/v)

LC/MS, calculated value of $C_{62}H_{89}N_{11}O_{14}S_4$ 1339.55, measured value of 1338.6

Example 4: Synthesis of Compound 4 in Accordance with Exemplary Embodiments of the Present Invention

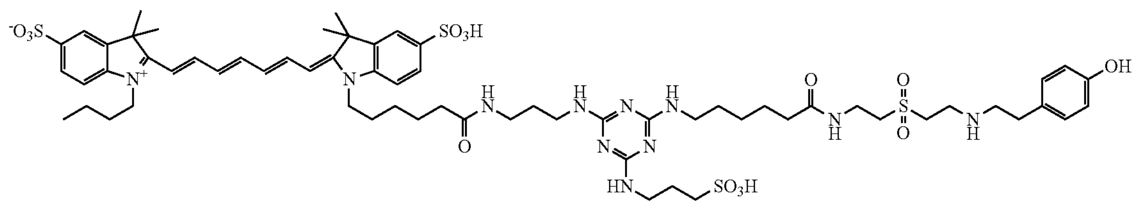

4

The compound 4 was obtained by applying the method described in example 1 except using Flamma 749 Carboxylic acid (BioActs) instead of the compound 1-13 in example 1 (73 mg, 42.8%).

$R_f$=0.23 (Silicagel, isobutanol/n-propanol/ethyl acetate/water 2:4:1:3 v/v/v/v)

LC/MS, calculated value of $C_{64}H_{91}N_{11}O_{14}S_4$ 1365.56, measured value of 1365.9

Example 5: Synthesis of Compound 5 in Accordance with Exemplary Embodiments of the Present Invention

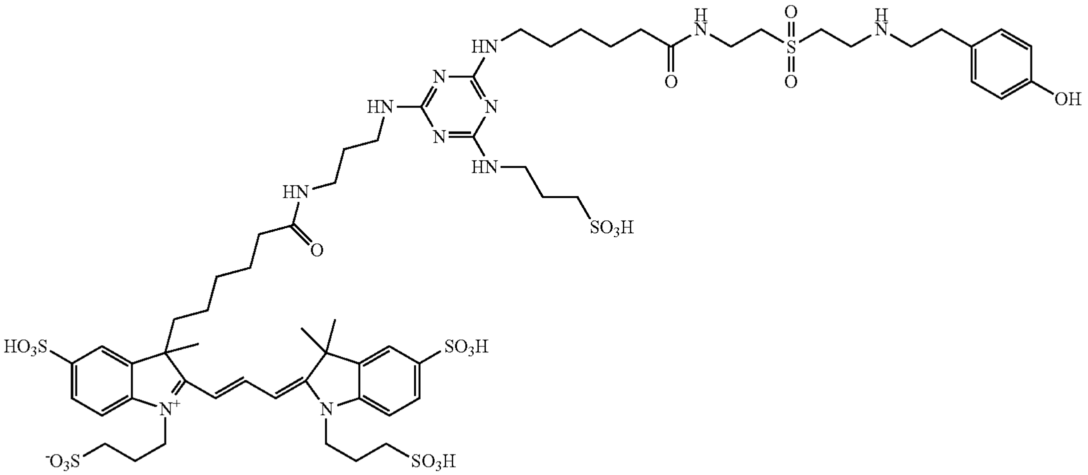

5

The compound 5 was obtained by applying the method described in example 1 except using malonaldehyde dianilide hydrochloride instead of glutaconaldehydedianil hydrochloride in preparing example 1-12 (11 mg, 23.4%).

$R_f$=0.23 (Silicagel, isobutanol/n-propanol/ethyl acetate/water 2:4:1:3 v/v/v/v)

LC/MS, calculated value of $C_{61}H_{89}N_{11}O_{20}S_6$ 1487.46, measured value of 1488.2

Example 6: Synthesis of Compound 6 in Accordance with Exemplary Embodiments of the Present Invention

6

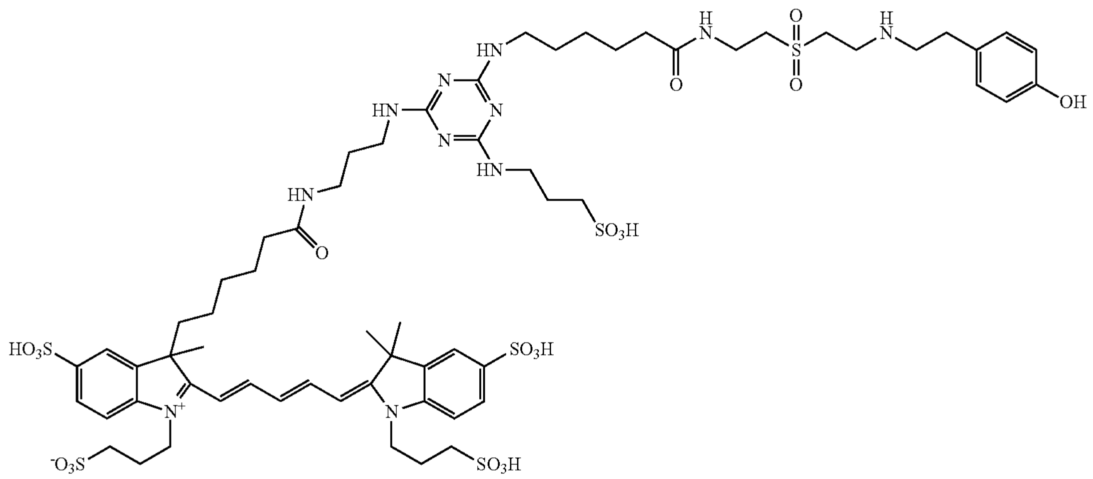

The compound 6 was obtained by applying the method described in example 1 except using malonaldehyde dianilide hydrochloride instead of glutaconaldehydedianil hydrochloride in preparing example 1-12 (11 mg, 23.4%).

$R_f$=0.23 (Silicagel, isobutanol/n-propanol/ethyl acetate/water 2:4:1:3 v/v/v/v)

LC/MS, calculated value of $C_{63}H_{91}N_{11}O_{20}S_6$ 1513.48, measured value of 1512.4

Example 7: Synthesis of Compound 7 in Accordance with Exemplary Embodiments of the Present Invention

7

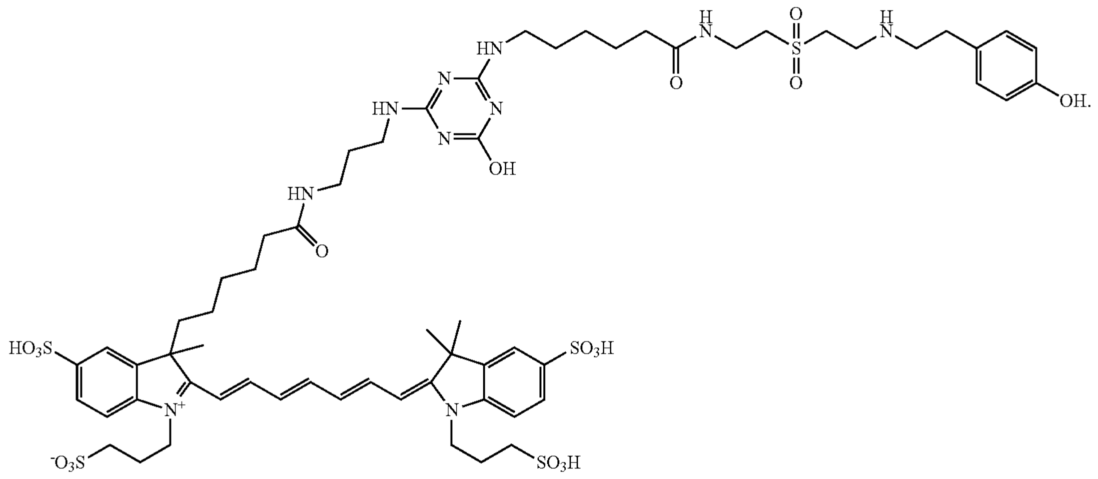

The compound 7 was obtained by applying the method described in example 1 except using the compounds 1-3 and 1-4 in preparing example 1-15 (9 mg, 12.1%).

$R_f$=0.25 (Silicagel, isobutanol/n-propanol/ethyl acetate/water 2:4:1:3 v/v/v/v)

LC/MS, calculated value of $C_{63}H_{88}N_{10}O_{18}S_5$ 1432.49, measured value of 1431.1

Example 8: Synthesis of Compound 8 in Accordance with Exemplary Embodiments of the Present Invention

8

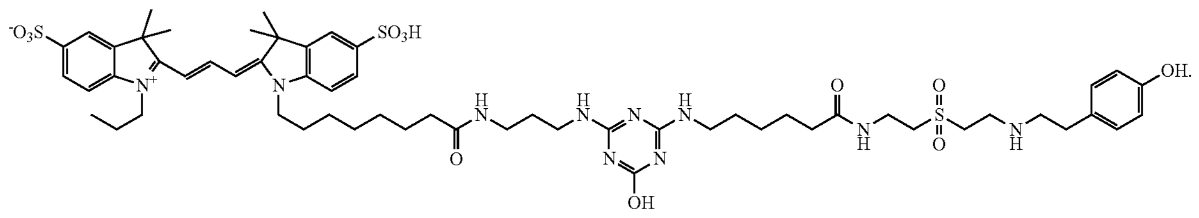

The compound 8 was obtained by applying the method described in example 1 except using Flamma 552 Carboxylic acid (BioActs) instead of the compound 1-13 in example 1 and using the compound 1-4 instead of the compound 1-3 in preparing example 1-15 (43.1 mg, 43.1%).

$R_f$=0.25 (Silicagel, isobutanol/n-propanol/ethyl acetate/water 2:4:1:3 v/v/v/v)

LC/MS, calculated value of $C_{58}H_{82}N_{10}O_{12}S_3$ 1206.53, measured value of 1205.5

Example 9: Synthesis of Compound 9 in Accordance with Exemplary Embodiments of the Present Invention

9

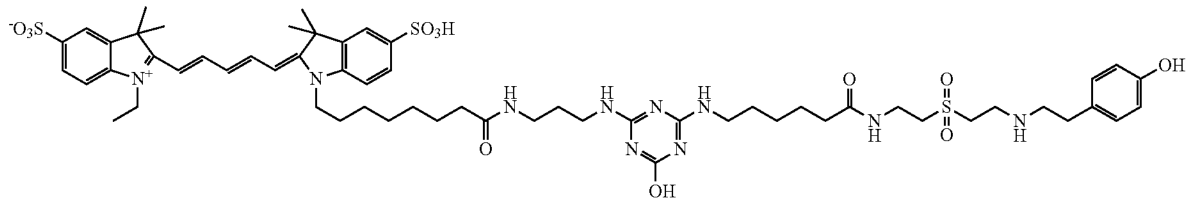

The compound 9 was obtained by applying the method described in example 1 except using Flamma 648 Carboxylic acid (BioActs) instead of the compound 1-13 in example 1 and using the compound 1-4 instead of the compound 1-3 in preparing example 1-15 (73 mg, 37.9%).

$R_f$=0.19 (Silicagel, isobutanol/n-propanol/ethyl acetate/water 2:4:1:3 v/v/v/v)

LC/MS, calculated value of $C_{59}H_{82}N_{10}O_{12}S_3$ 1218.53, measured value of 1217.3

Example 10: Synthesis of Compound 10 in Accordance with Exemplary Embodiments of the Present Invention

10

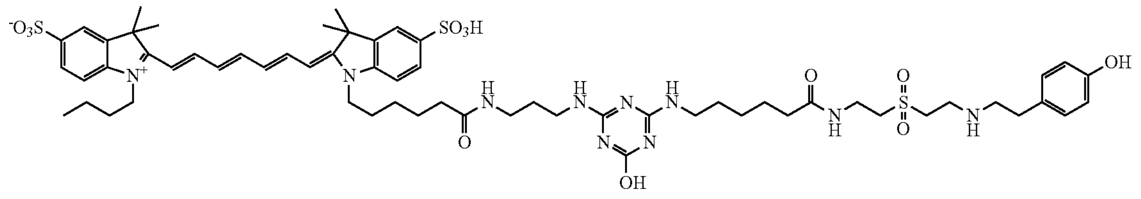

The compound 10 was obtained by applying the method described in example 1 except using Flamma 749 Carboxylic acid (BioActs) instead of the compound 1-13 in example 1 and using the compound 1-4 instead of the compound 1-3 in preparing example 1-15 (41 mg, 21.7%).

$R_f$=0.18 (Silicagel, isobutanol/n-propanol/ethyl acetate/water 2:4:1:3 v/v/v/v)

LC/MS, calculated value of $C_{61}H_{84}N_{10}O_{12}S_3$ 1244.54, measured value of 1243.9

Example 11: Synthesis of Compound 11 in Accordance with Exemplary Embodiments of the Present Invention

11

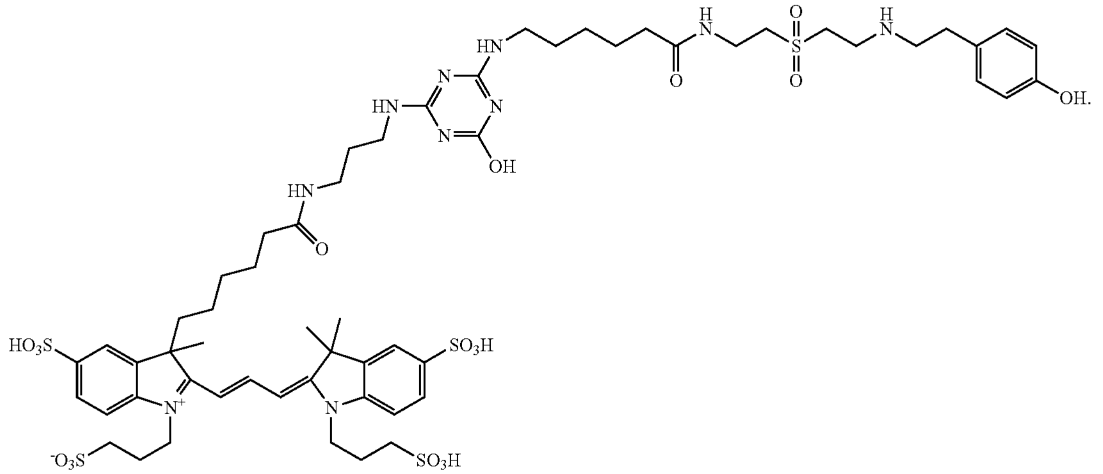

The compound 11 was obtained by applying the method described in example 1 except using N,N'-Diphenylformamidine instead of glutaconaldehydedianil hydrochloride in preparing example 1-12 and using the compound 1-4 instead of the compound 1-3 in preparing example 1-15 (41 mg, 21.7%). (3.1 mg, 17.2%)

$R_f$=0.17 (Silicagel, isobutanol/n-propanol/ethyl acetate/water 2:4:1:3 v/v/v/v)

LC/MS, calculated value of $C_{58}H_{82}N_{10}O_{18}S_5$ 1366.44, measured value of 1365.2

Example 12: Synthesis of Compound 12 in Accordance with Exemplary Embodiments of the Present Invention

12

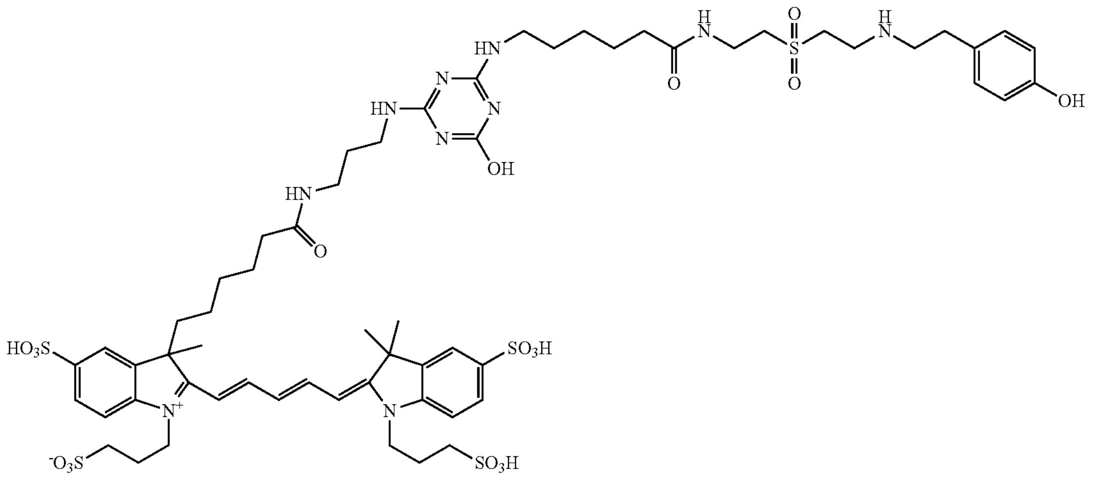

The compound 12 was obtained by applying the method described in example 1 except using malonaldehyde dianilide hydrochloride instead of glutaconaldehydedianil hydrochloride in preparing example 1-12. (6.2 mg, 10.8%)

$R_f$=0.21 (Silicagel, isobutanol/n-propanol/ethyl acetate/water 2:4:1:3 v/v/v/v)

LC/MS, calculated value of $C_{60}H_{84}N_{10}O_{18}S_5$ 1392.46, measured value of 1391.4

Testing Example 1: Performance-Testing of the TSA (Tyramide Signal Amplification) Solution Prepared from the Compound 1

(1) Preparing TSA Solution

The compound 1 and 4-iodophenylboronic acid was dissolved in dimethyl sulfoxide respectively and TSA solution was prepared by mixing the solutions with the ratio of 1:5.

(2) Preparing Tissue Samples

Rat kidney tissue was immobilized in formaldehyde solution during a night. Then paraffin embedding block was manufactured by a standard manufacturing method of tissue samples. The embedding block was sliced in 4 um and attached on slide glass.

Then slide for immunohistochemistry was manufactured by removing paraffin through xylene.

(3) Tyramide Immunohistochemistry

After the slide prepared in (2) was deparaffinized and remoisturized, the slide was treated with tris-EDTA buffer (pH 9.0, 100° C., 30 min) and microwaved (750 W, 5 min, 4 times). Then the slide was exposed on light source.

Anti-CD3 as a first antibody (Abcam, ab16669) was diluted with ratio of 1:100 and treated in 30 min. Mouse/Rabbit IgG HRP as a second antibody (R&D systems, VC002-125) was diluted with ratio of 1:5000 and treated in 10 min.

The antibodies were treated with the TSA solution with the dilution ratio 1:150 prepared in (1) for 10 min. After the step of antigen retrieval by tris-EDTA buffer (pH 6.0), the slide was treated by DAPI (Thermo, 62248) with the dilution ratio 1:1000 for observing the nucleus inside of the tissue sample.

After washing the slide, the slide was mounted by using ProLong Gold antifade reagent (Invitrogen, P36934).

(4) Photographing Fluorescent Image

The slide mounted and immuno-stained with tyramide was scanned through automatic quantitative pathology analysis system (Akoya Bioscience, Vectra polaris automated quantitative pathology imaging system) with the filter 780 (excitation: 715-765, emission: 765-900) and the result was showed in FIG. 1.

It is verified that the tissue sample can be analyzed with the TSA solution prepared from the compound 1 with fluorescence filter 780.

FIG. 2 is the illustration which compares the principle of TSA method in testing example 1 (left) and prior ELISA method (right).

The TSA (Tyramide signal amplification) as a method of multiplex immunohistochemical staining in the present invention is used for effective detection of protein, antibody, DNA, RNA, etc as the low concentrated biochemical targets.

TSA method makes the amplification of fluorescent signal possible by activating TSA fluorescent probe with HRP (horseradish peroxidase) enzyme.

In TSA method, a second antibody bonded with HRP enzyme for detecting a first antibody attaching target chemical is attached into TSA fluorescent probe. The second antibody can amplify the fluorescent signal by attaching tyrosine close to it.

The advantage of TSA method is that the detection of low concentrated target is possible by fluorescence amplification compared to prior methods such as ELISA (enzyme-linked immunosorbent assay), ICC (Immuno CytoChemistry), IHC (Immunohistochemistry), FISH (fluorescence in situ hybridzation), etc.

While ELISA detects antigen by fluorescent second antibody, TSA can detect target by infinite fluorescence amplification through HRP bonded with a second antibody. It is possible to simultaneously collect complex fluorescent images by applying TSA method repeatedly. When applied to prior ELISA-type experiments, TSA method can detect various biomarkers respectively with only one experiment.

The activated TSA fluorescent chemical attaches to tyrosine close to it because of easy-deactivation by water and reduces background noise because it is deactivated when isolated from antigen.

Because it is easy to amplify TSA fluorescent chemical by only replacing a second antibody in ELISA by the second antibody attached with HRP-TSA fluorescent chemical, TSA method can be easily applied to prior bio-methods, especially for detecting low concentration of virus, such as Corona and bacteria.

The present invention is not limited by the above-described embodiments, and various modifications and changes can be made by those skilled in the art and may be used in various biological and chemical fields, and are included in the spirit and scope of the present invention as defined in the appended claims.

The invention claimed is:

1. A fluorescent compound for labeling a biomaterial having the following Chemical Formula 1:

[Chemical Formula 1]

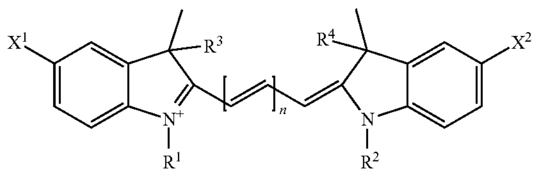

In Chemical Formula 1 above, n is an integer of 1 to 3, $X^1$ and $X^2$ are the same as or different from each other, and each independently selected from H, $—SO_3$ and $—SO_3H$, either i) one of $R^1$ and $R^2$ is $—(CH_2)_{m1}SO_3^-$ or $—(CH_2)_{m2}SO_3H$, and the other one is

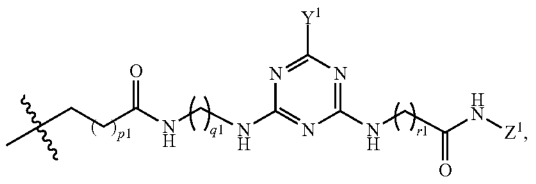

and $R^3$ and $R^4$ are the same or different from each other and independently selected from substituted or unsubstituted $C_{1-7}$ alkyl, or ii) $R^1$ and $R^2$ are the same or different from each other and independently selected from —$(CH_2)_{m1}SO_3$ or —$(CH_2)_{m2}SO_3H$, and one of $R^3$ and $R^4$ is substituted or unsubstituted $C_{1-7}$alkyl, and the other one is

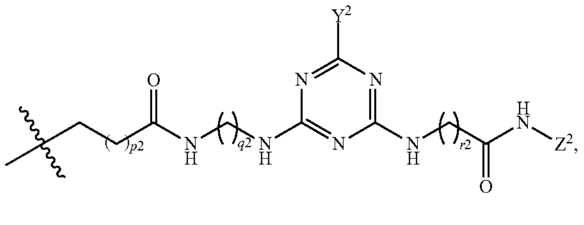

m1 is an integer of 1 to 5, m2 is an integer of 1 to 5, p1 is an integer of 1 to 5, q1 is an integer of 0 to 6, r1 is an integer of 1 to 6, and $Y^1$ is selected from H, —OH, halogen and

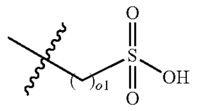

o1 is an integer of 1 to 10, $Z^1$ is selected from H, $C_{1-7}$ alkyl, substituted or unsubstituted $C_{8-20}$ alkyl and

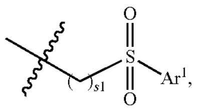

s1 is an integer of 1 to 10, and $Ar^1$ is selected from H, $C_{1-7}$ alkyl, substituted or unsubstituted $C_{8-20}$ alkyl, $C_{1-7}$ aminoalkyl and

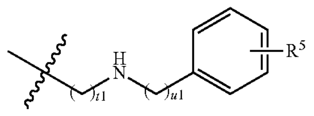

t1 is an integer of 1 to 10, u1 is an integer of 1 to 10, and $R_5$ is selected from H, OH, $C_{1-7}$ alkyl, substituted or unsubstituted $C_{8-20}$ alkyl, and p2 is an integer of 1 to 5, q2 is an integer of 1 to 5, r2 is an integer of 1 to 6, and $Y^2$ is selected from H, —OH, halogen and

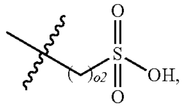

o2 is an integer of 1 to 10, $Z^2$ is selected from H, substituted or unsubstituted $C_{1-7}$ alkyl, substituted or unsubstituted $C_{8-20}$ alkyl and

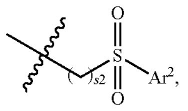

s2 is an integer of 1 to 10, and $Ar^2$ is selected from H, substituted or unsubstituted $C_{1-7}$ alkyl, substituted or unsubstituted $C_{8-20}$ alkyl, $C_{1-7}$ aminoalkyl and

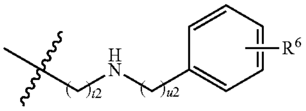

and t2 is an integer of 1 to 4, u2 is an integer of 1 to 4, $R^6$ is selected from H, —OH, substituted or unsubstituted $C_{1-7}$ alkyl and substituted or unsubstituted $C_{8-20}$ alkyl.

2. The fluorescent compound of claim 1, wherein the compound of Chemical Formula 1 above is any one selected from compounds represented by the following Chemical Formulas 1-12:

1
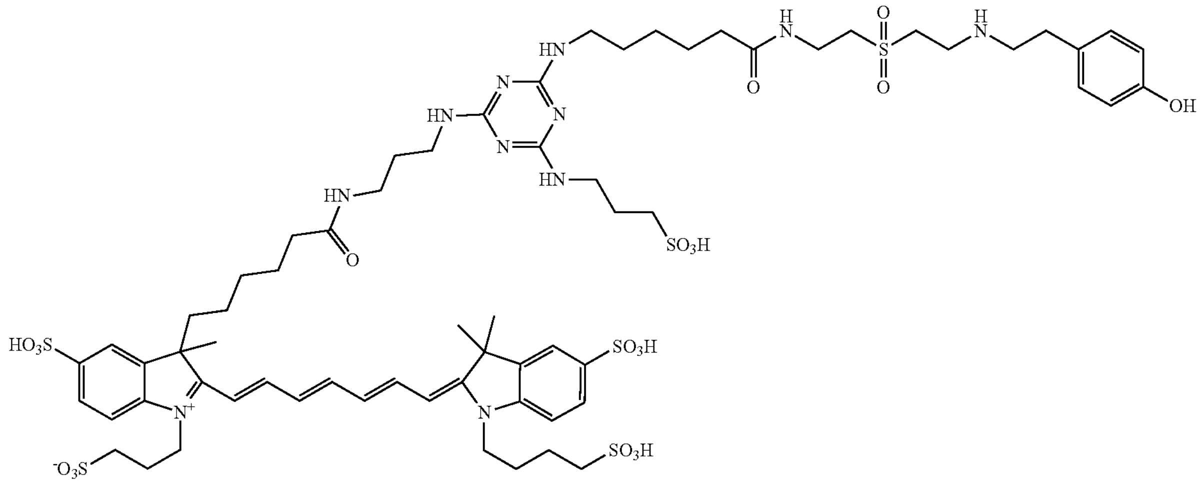
2
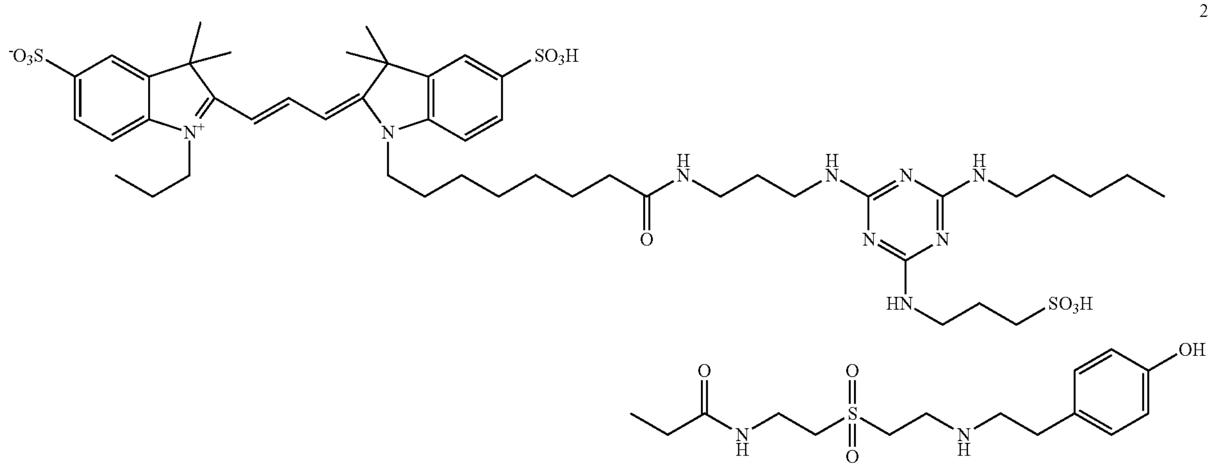
3
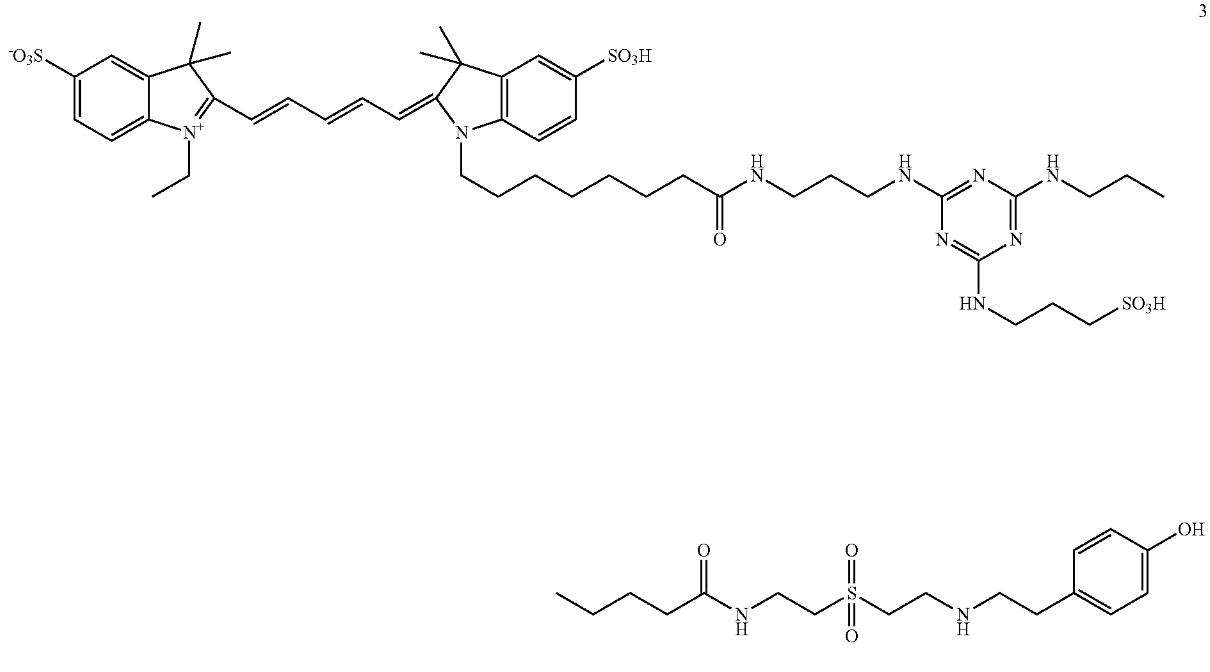

-continued
4
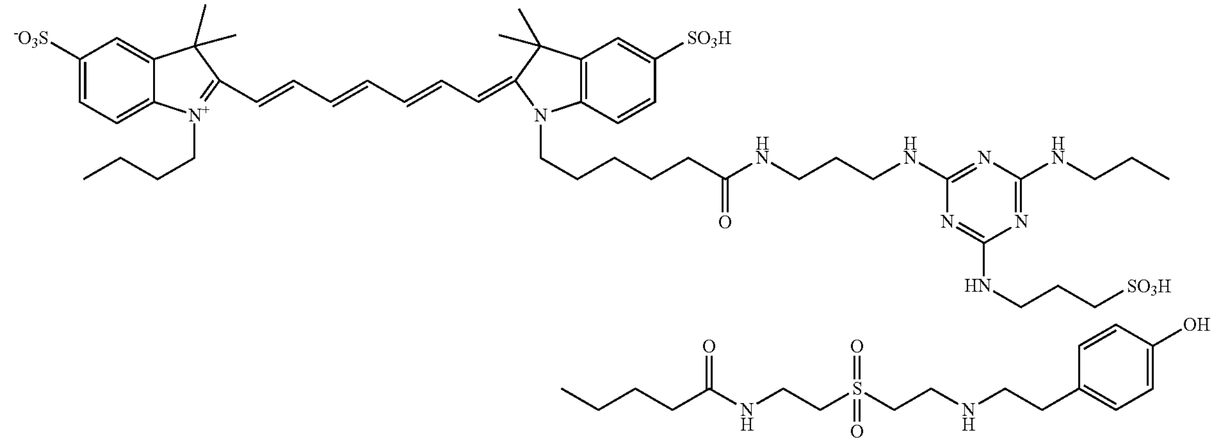
5
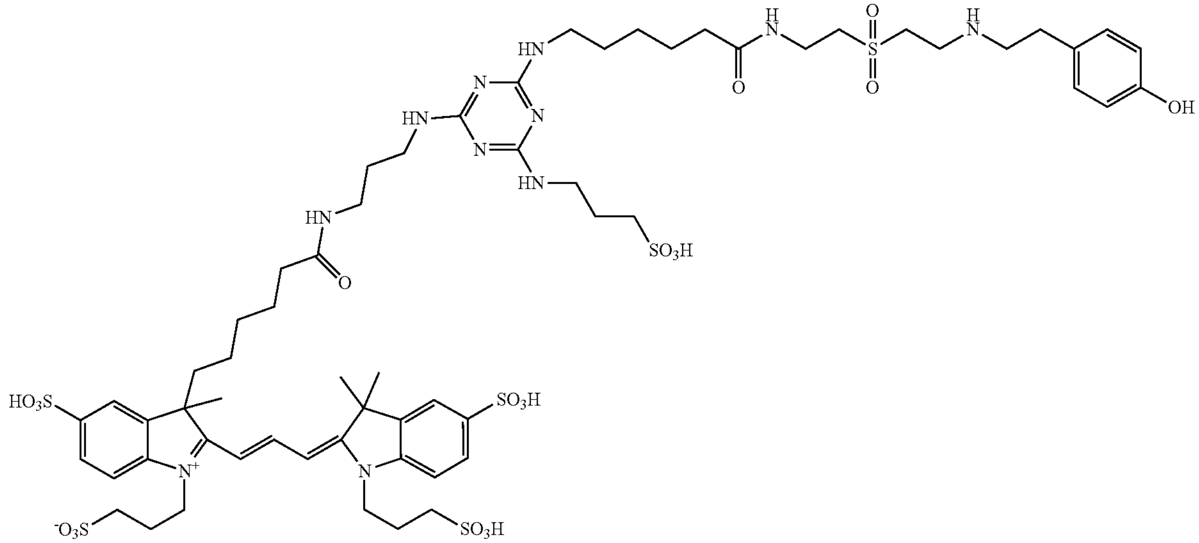
6
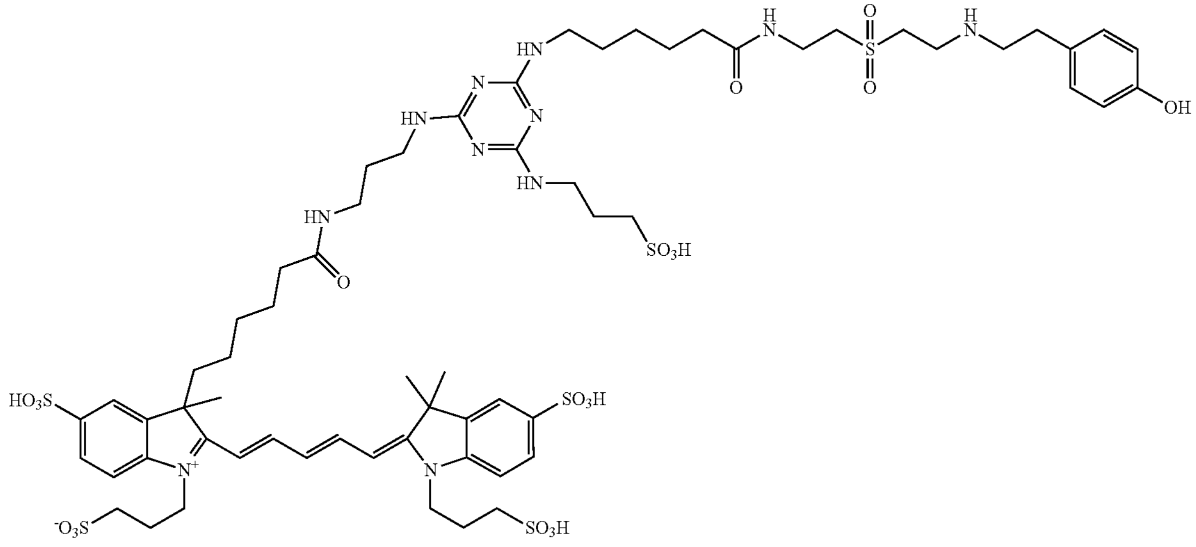

-continued
7
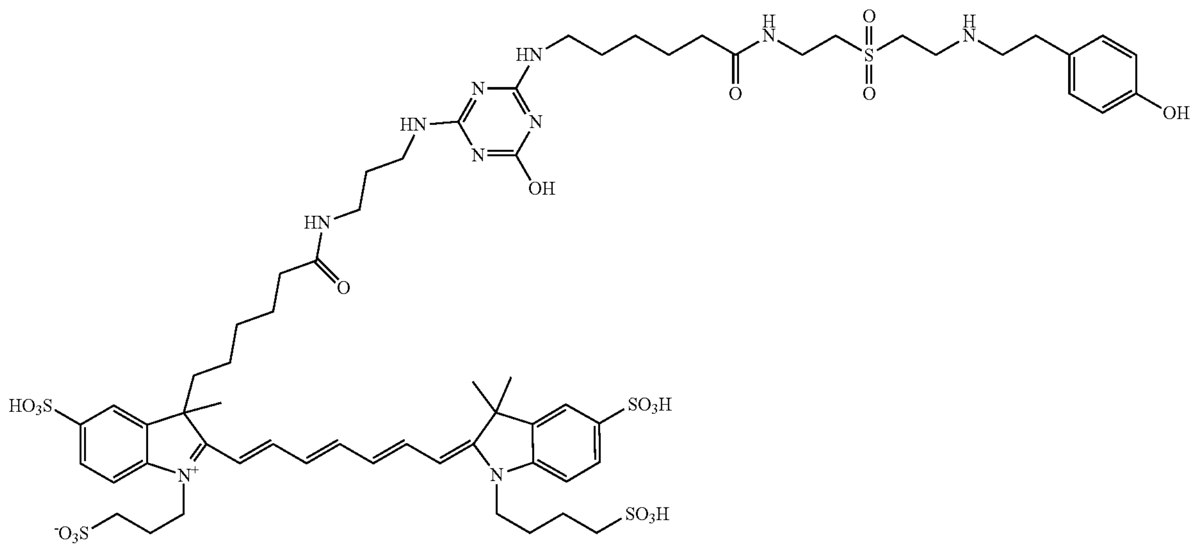
8
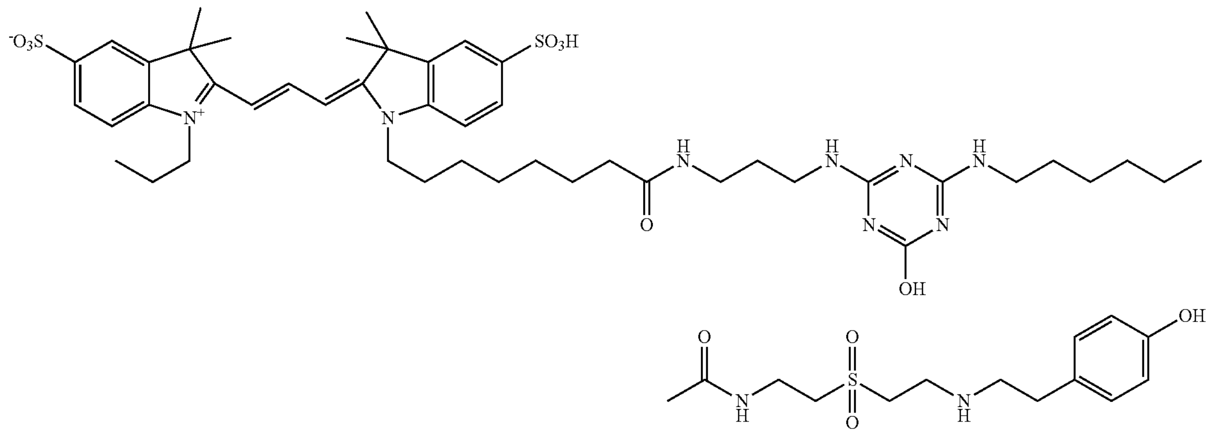
9
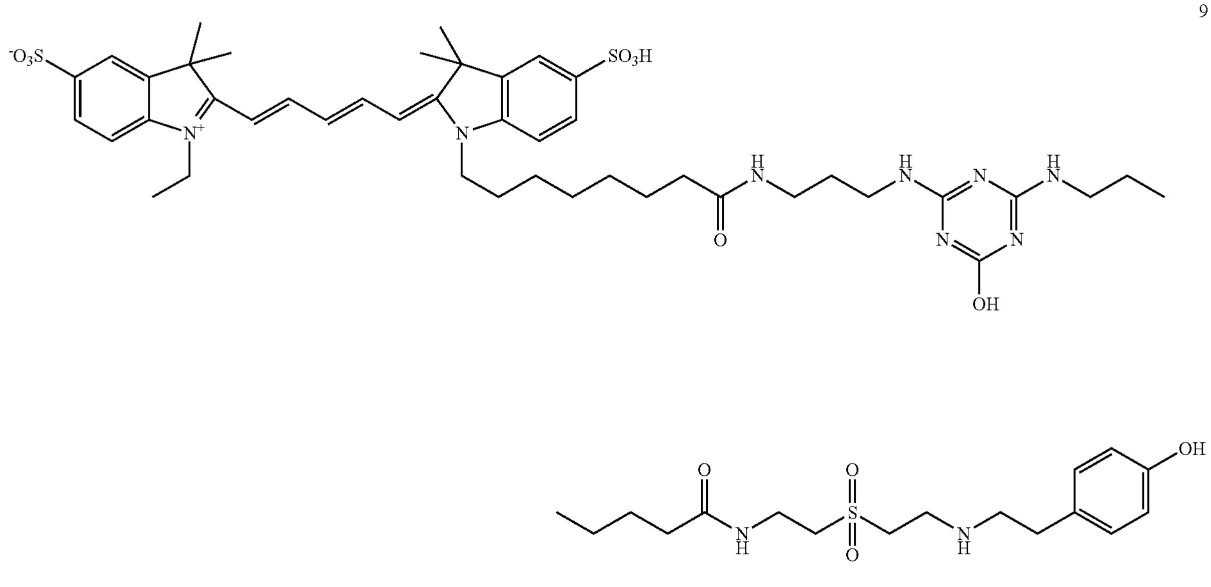

-continued
10
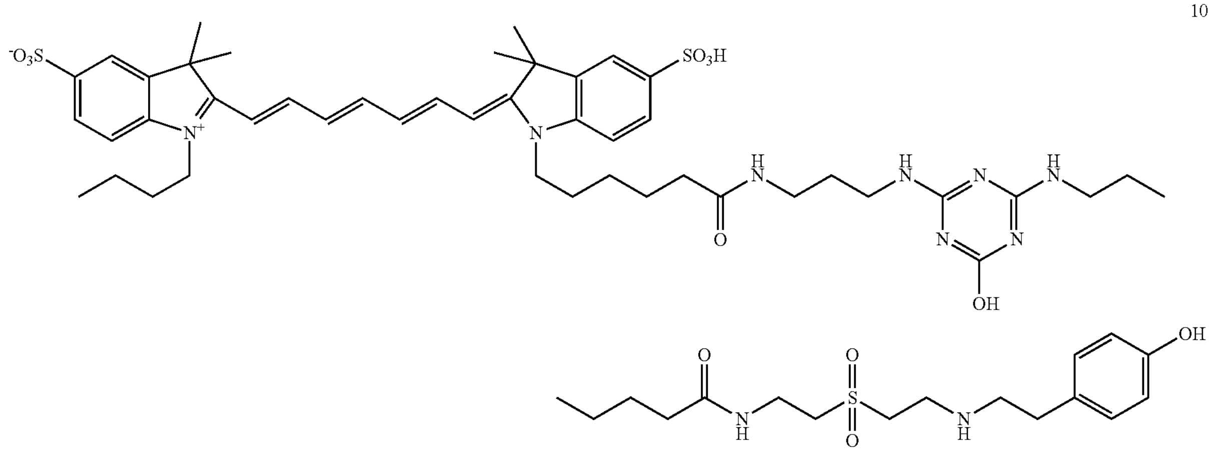
11
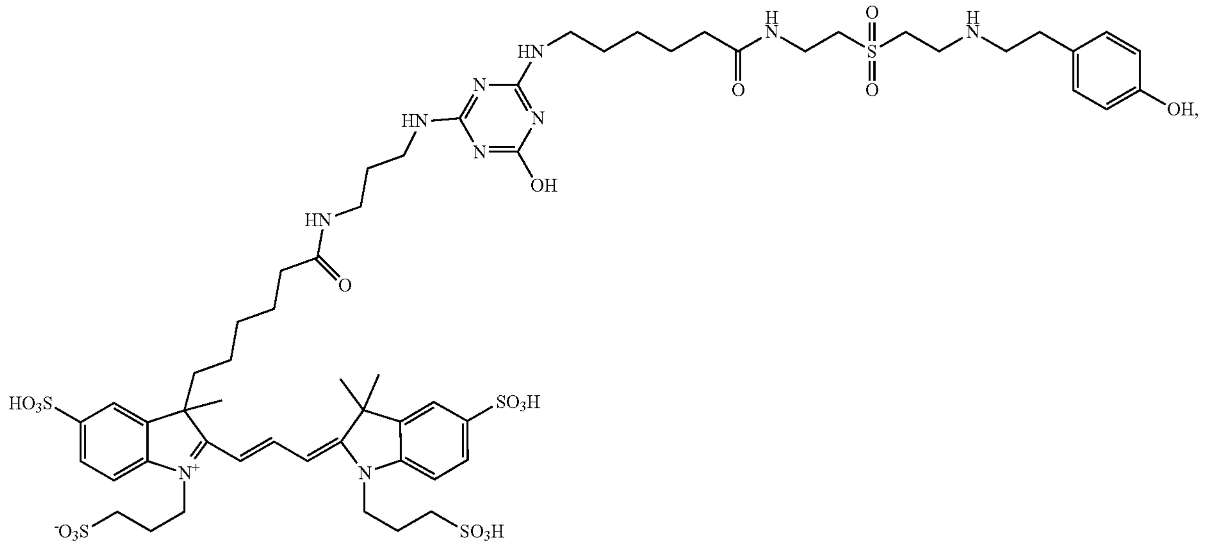
12
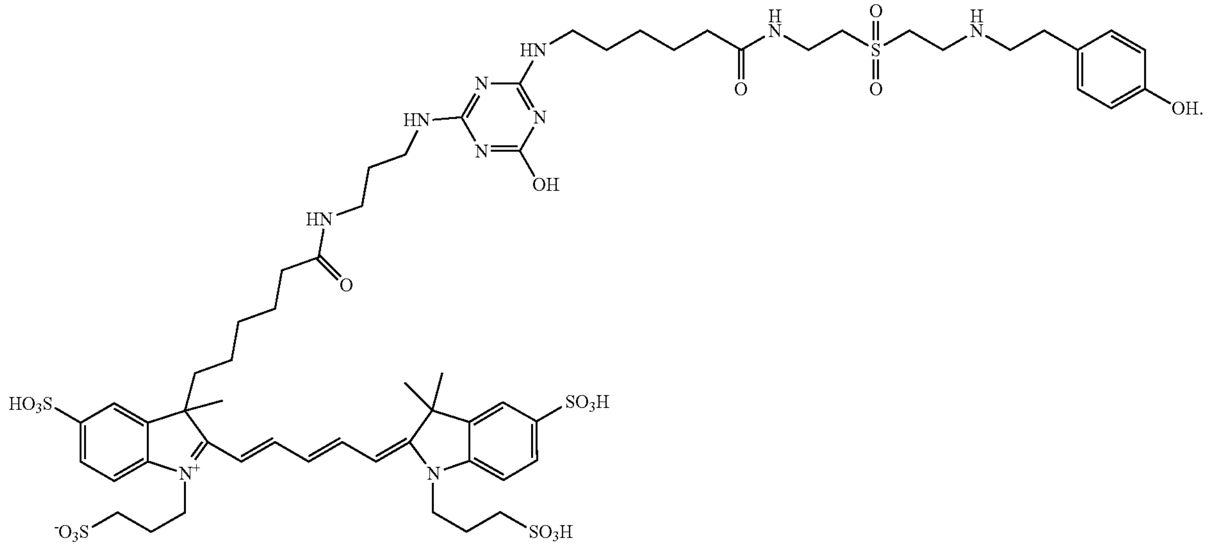

3. The fluorescent compound of claim 1, wherein the compound is for immunohistochemistry.

4. The fluorescent compound of claim 1, wherein the compound is for immunohistochemistry which simultaneously stains multiple markers.

5. An immunohistochemical composition for detecting a biomaterial comprising a fluorescent compound represented by the following Chemical Formula 1:

[Chemical Formula 1]

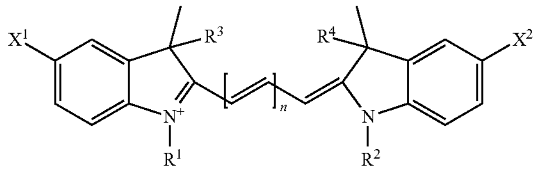

In Chemical Formula 1 above, n is an integer of 1 to 3, $X^1$ and $X^2$ are the same as or different from each other, and each independently selected from H, $—SO_3^-$ and $—SO_3H$, either i) one of $R^1$ and $R^2$ is $—(CH_2)_{m1}SO_3$ or $—(CH_2)_{m2}SO_3H$, and the other one is

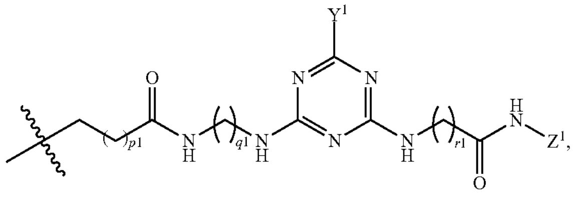

and $R^3$ and $R^4$ are the same or different from each other and independently selected from substituted or unsubstituted $C_{1-7}$ alkyl, or ii) $R^1$ and $R^2$ are the same or different from each other and independently selected from $—(CH_2)_{m1}SO_3$ or $—(CH_2)_{m2}SO_3H$, and one of $R^3$ and $R^4$ should be substituted or unsubstituted $C_{1-7}$ alkyl, and the other one is

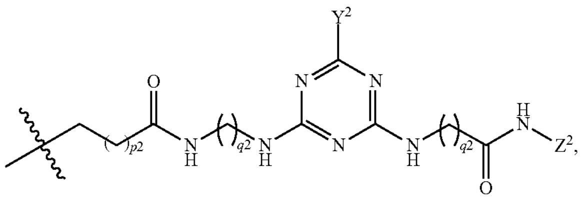

m1 is an integer of 1 to 5, m2 is an integer of 1 to 5, p1 is an integer of 1 to 5, q1 is an integer of 0 to 6, r1 is an integer of 1 to 6, and $Y^1$ is selected from H, —OH, halogen and

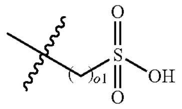

o1 is an integer of 1 to 10, $Z^1$ is selected from H, $C_{1-7}$ alkyl, substituted or unsubstituted $C_{8-20}$ alkyl and

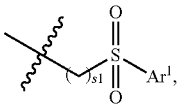

s1 is an integer of 1 to 10, and $Ar^1$ is selected from H, $C_{1-7}$ alkyl, substituted or unsubstituted $C_{8-20}$ alkyl, $C_{1-7}$ aminoalkyl and

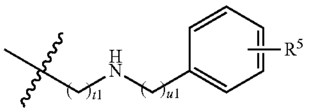

t1 is an integer of 1 to 10, u1 is an integer of 1 to 10, and $R^5$ is selected from H, OH, $C_{1-7}$ alkyl, substituted or unsubstituted $C_{8-20}$ alkyl, and p2 is an integer of 1 to 5, q2 is an integer of 1 to 5, r2 is an integer of 1 to 6, and $Y^2$ is selected from H, —OH, halogen and

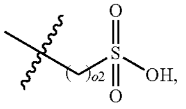

o2 is an integer of 1 to 10, $Z^2$ is selected from H, substituted or unsubstituted $C_{1-7}$ alkyl, substituted or unsubstituted $C_{8-20}$ alkyl and

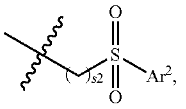

s2 is an integer of 1 to 10, and $Ar^2$ is selected from H, substituted or unsubstituted $C_{1-7}$ alkyl, substituted or unsubstituted $C_{8-20}$ alkyl, $C_{1-7}$ aminoalkyl and

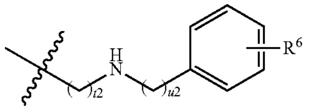

and t2 is an integer of 1 to 4, u2 is an integer of 1 to 4, $R^6$ is selected from H, —OH, substituted or unsubstituted $C_{1-7}$ alkyl and substituted or unsubstituted $C_{8-20}$ alkyl.

* * * * *